United States Patent
Teller

(10) Patent No.: US 9,439,563 B2
(45) Date of Patent: *Sep. 13, 2016

(54) MEASUREMENT METHOD AND SYSTEM

(71) Applicant: Google Inc., Mountain View, CA (US)

(72) Inventor: Eric Teller, San Francisco, CA (US)

(73) Assignee: Google Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/524,753

(22) Filed: Oct. 27, 2014

(65) Prior Publication Data

US 2015/0042953 A1 Feb. 12, 2015

Related U.S. Application Data

(63) Continuation of application No. 13/292,909, filed on Nov. 9, 2011, now Pat. No. 8,879,155.

(51) Int. Cl.
*G02B 27/14* (2006.01)
*G02B 1/00* (2006.01)
(Continued)

(52) U.S. Cl.
CPC ............ *A61B 3/113* (2013.01); *G02B 27/017* (2013.01); *G02B 27/14* (2013.01); *G06F 3/013* (2013.01); *G06K 9/00604* (2013.01); *H04H 60/33* (2013.01); *H04H 60/46* (2013.01); *G02B 27/0093* (2013.01); *G02B 2027/014* (2013.01); *G02B 2027/0138* (2013.01); *G02B 2027/0178* (2013.01); *G02B 2027/0187* (2013.01)

(58) Field of Classification Search
USPC .............. 359/630–634, 13; 351/200–246
See application file for complete search history.

(56) References Cited

U.S. PATENT DOCUMENTS 5,583,795 A 12/1996 Smyth
6,601,021 B2 * 7/2003 Card ...................... G06F 3/013
340/3.6

(Continued)

FOREIGN PATENT DOCUMENTS

WO 2007027456 3/2007
WO 2009143564 12/2009
(Continued)

OTHER PUBLICATIONS

Starner, Thad; "The Challenges of Wearable Computing: Part 1"; Georgia Institute of Technology; IEEE; Jul.-Aug. 2001, pp. 44-52.
(Continued)

*Primary Examiner* — Mohammed Hasan
(74) *Attorney, Agent, or Firm* — McDonnell Boehnen Hulbert & Berghoff

(57) ABSTRACT

Methods and systems for determining an individual gaze value are disclosed herein. An exemplary method involves: (a) receiving gaze data for a first wearable computing device, wherein the gaze data is indicative of a wearer-view associated with the first wearable computing device, and wherein the first wearable computing device is associated with a first user-account; (b) analyzing the gaze data from the first wearable computing device to detect one or more occurrences of one or more advertisement spaces in the gaze data; (c) based at least in part on the one or more detected advertisement-space occurrences, determining an individual gaze value for the first user-account; and (d) sending a gaze-value indication, wherein the gaze-value indication indicates the individual gaze value for the first user-account.

20 Claims, 11 Drawing Sheets

(51) Int. Cl.
    *A61B 3/113*     (2006.01)
    *G02B 27/01*     (2006.01)
    *G06F 3/01*     (2006.01)
    *H04H 60/33*     (2008.01)
    *H04H 60/46*     (2008.01)
    *G06K 9/00*     (2006.01)
    *G02B 27/00*     (2006.01)

(56) References Cited

U.S. PATENT DOCUMENTS

| | | | |
|---|---|---|---|
| 7,996,264 B2 | 8/2011 | Kusumoto et al. | |
| 8,136,944 B2* | 3/2012 | De Lemos | A61B 3/113 351/209 |
| 8,873,147 B1* | 10/2014 | Rhodes | G02B 27/0172 359/630 |
| 8,879,155 B1* | 11/2014 | Teller | G06K 9/00604 359/13 |
| 8,957,916 B1* | 2/2015 | Hedman | G09G 5/00 345/633 |
| 2002/0085843 A1 | 7/2002 | Mann | |
| 2006/0256133 A1 | 11/2006 | Rosenberg | |
| 2007/0098234 A1 | 5/2007 | Fiala | |
| 2007/0182812 A1 | 8/2007 | Ritchey | |
| 2008/0147488 A1 | 6/2008 | Tunick et al. | |
| 2009/0019472 A1 | 1/2009 | Cleland et al. | |
| 2009/0062629 A1 | 3/2009 | Pradeep et al. | |
| 2009/0177528 A1 | 7/2009 | Wu et al. | |
| 2009/0238378 A1 | 9/2009 | Kikinis et al. | |
| 2010/0191631 A1 | 7/2010 | Weidmann | |
| 2011/0004481 A1 | 1/2011 | Jones | |
| 2011/0085700 A1 | 4/2011 | Lee | |
| 2011/0161160 A1 | 6/2011 | Carlson et al. | |
| 2011/0161163 A1 | 6/2011 | Carlson et al. | |
| 2011/0166942 A1 | 7/2011 | Vassilvitskii et al. | |
| 2011/0213664 A1 | 9/2011 | Osterhout et al. | |
| 2011/0234475 A1 | 9/2011 | Endo | |
| 2011/0258049 A1 | 10/2011 | Ramer et al. | |
| 2012/0075168 A1 | 3/2012 | Osterhout et al. | |
| 2012/0229909 A1 | 9/2012 | Clavin et al. | |
| 2013/0106674 A1 | 5/2013 | Wheeler et al. | |

FOREIGN PATENT DOCUMENTS

| | | |
|---|---|---|
| WO | 2010/060146 | 6/2010 |
| WO | 2010060146 | 6/2010 |

OTHER PUBLICATIONS

Starner, Thad; "The Challenges of Wearable Computing: Part 2"; Georgia Institute of Technology; IEEE; Jul.-Aug. 2001, pp. 54-67.
Starner, Thad; "The Challenges of Wearable Computing: Part 1"; Georgia Institute of Technology; IEEE; Jul.-Aug. 2001.
Starner, Thad; "The Challenges of Wearable Computing: Part 2"; Georgia Institute of Technology; IEEE; Jul.-Aug. 2001.
Hartberger, R. H&C Coffee History. Quality Coffee Company. 2006. Web. Mar. 4, 2010. <http://www.qualitycoffee.com/hchistory.htm>.
Loeffler, W. 100 years later, neon still glowing bright. McClatchy—Tribune Business News. Nov. 9, 2008. Web. Dec. 5, 2013 <http://search.proquest.com/docview/456859242?accountid=14753>.
MacKie, John. "Signs from Vancouver's Neon Age Stand the Test of Time." The Vancouver Sun; 0. Oct. 6, 2003. ProQuest. Web. Dec. 5, 2013 <http://search.proquest.com/docview/242386453?acciybtud=14753>.
Mullen, M. Heinz to Light Up the Night With Refurbished Ketchup Sign. Heinz Online Newsroom. Nov. 5, 2007. Business Wire. Web. Dec. 5, 2013 <http://news.heinz.com/press-release/general/heinz-light-night-refurbishedketchup-sign>.
Unpublished U.S. Appl. No. 13/292,898, filed Nov. 9, 2011 entitled "Marketplace for Advertising Space Using Gaze-Data Valuation".
Unpublished U.S. Appl. No. 13/292,904, filed Nov. 9, 2011 entitled "Real-Time Targeting of Advertisements Based on Gaze Direction".
Unpublished U.S. Appl. No. 13/292,909, filed Nov. 9, 2011 entitled "Individualized Gaze Valuation Based on Gaze Data".
Unpublished U.S. Appl. No. 13/428,964, filed Mar. 23, 2012 entitled "Gaze-Data Based Targeting of Advertising in Wearable Display".
Unpublished U.S. Appl. No. 13/474,970, filed May 18, 2012 entitled "Real-Time Trading of Gaze-Based Advertisement Opportunities".
Unpublished U.S. Appl. No. 13/428,979, filed Mar. 23, 2012 entitled "Feedback to Inform of Learnt Advertising Preferences".
Unpublished U.S. Appl. No. 13/478,218, filed May 23, 2012 entitled "Removal of Biometric Data from Gaze Data".
Unpublished U.S. Appl. No. 13/428,991, filed Mar. 23, 2012 entitled "Placement of Advertisements in See-Through Display of a Head-Mountable Device".
Unpublished U.S. Appl. No. 13/472,902, filed May 16, 2012 entitled "Audio Advertisements Based on Gaze Information".
Unpublished U.S. Appl. No. 13/419,783, filed Mar. 14, 2012 entitled "Distributing Advertisements in a Wearable Display".
Unpublished U.S. Appl. No. 13/292,893, filed Nov. 9, 2011 entitled "Valuing Advertisement Space Based on Gaze Data".

* cited by examiner

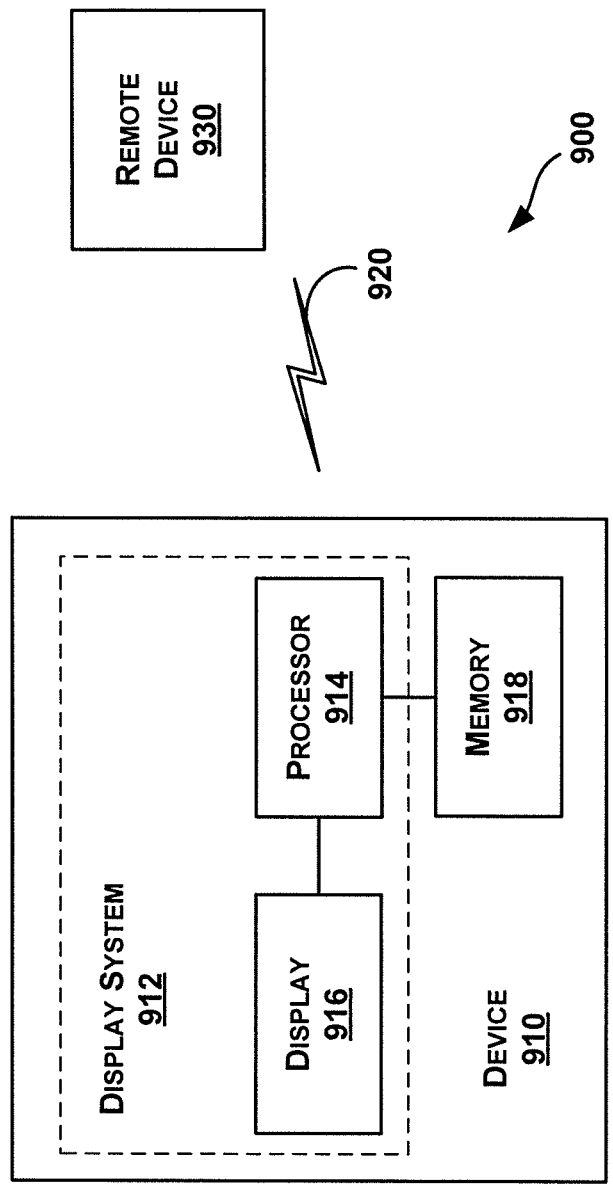

MEASUREMENT METHOD AND SYSTEM

CROSS-REFERENCE TO RELATED APPLICATIONS

The present disclosure is a continuation of co-owned U.S. patent application Ser. No. 13/292,909, Now U.S. Pat. No. 8,879,155 B2 filed on Nov. 9, 2011, which is herein incorporated by reference in its entirety.

BACKGROUND

Unless otherwise indicated herein, the materials described in this section are not prior art to the claims in this application and are not admitted to be prior art by inclusion in this section.

Computing devices such as personal computers, laptop computers, tablet computers, cellular phones, and countless types of Internet-capable devices are increasingly prevalent in numerous aspects of modern life. Over time, the manner in which these devices are providing information to users is becoming more intelligent, more efficient, more intuitive, and/or less obtrusive.

The trend toward miniaturization of computing hardware, peripherals, as well as of sensors, detectors, and image and audio processors, among other technologies, has helped open up a field sometimes referred to as "wearable computing." In the area of image and visual processing and production, in particular, it has become possible to consider wearable displays that place a very small image display element close enough to a wearer's (or user's) eye(s) such that the displayed image fills or nearly fills the field of view, and appears as a normal sized image, such as might be displayed on a traditional image display device. The relevant technology may be referred to as "near-eye displays."

Near-eye displays are fundamental components of wearable displays, also sometimes called "head-mounted displays" (HMDs). A head-mounted display places a graphic display or displays close to one or both eyes of a wearer. To generate the images on a display, a computer processing system may be used. Such displays may occupy a wearer's entire field of view, or only occupy part of wearer's field of view. Further, head-mounted displays may be as small as a pair of glasses or as large as a helmet.

Emerging and anticipated uses of wearable displays include applications in which users interact in real time with an augmented or virtual reality. Such applications can be mission-critical or safety-critical, such as in a public safety or aviation setting. The applications can also be recreational, such as interactive gaming.

SUMMARY

In one aspect, an exemplary computer-implemented method may involve: (a) receiving gaze data for a first wearable computing device, wherein the gaze data is indicative of a wearer-view associated with the first wearable computing device, and wherein the first wearable computing device is associated with a first user-account; (b) analyzing the gaze data from the first wearable computing device to detect one or more occurrences of one or more advertisement spaces in the gaze data; (c) based at least in part on the one or more detected advertisement-space occurrences, determining an individual gaze value for the first user-account; and (d) sending a gaze-value indication, wherein the gaze-value indication indicates the individual gaze value for the first user-account.

In another aspect, an exemplary system may include a non-transitory computer-readable medium and program instructions stored on the non-transitory computer-readable medium. The program instructions may be executable by at least one processor to: (a) receive gaze data for a first wearable computing device, wherein the gaze data is indicative of a wearer-view associated with the first wearable computing device, and wherein the first wearable computing device is associated with a first user-account; (b) analyze the gaze data from the first wearable computing device to detect one or more occurrences of one or more advertisement spaces in the gaze data; (c) based at least in part on the one or more detected advertisement-space occurrences, determine an individual gaze value for the first user-account; and (d) send a gaze-value indication, wherein the gaze-value indication indicates the individual gaze value for the first user-account.

In yet another aspect, an exemplary article of manufacture may include a computer-readable storage medium having instructions stored thereon that, in response to execution by a processor, cause the processor to perform operations. The instructions may include: (a) instructions for receiving gaze data for a first wearable computing device, wherein the gaze data is indicative of a wearer-view associated with the first wearable computing device, and wherein the first wearable computing device is associated with a first user-account; (b) instructions for analyzing the gaze data from the first wearable computing device to detect one or more occurrences of one or more advertisement spaces in the gaze data; (c) instructions for based at least in part on the one or more detected advertisement-space occurrences, determining an individual gaze value for the first user-account; and (d) instructions for sending a gaze-value indication, wherein the gaze-value indication indicates the individual gaze value for the first user-account.

In a further aspect, an exemplary computer-implemented method may involve: (a) receiving gaze data for a first wearable computing device, wherein the gaze data is indicative of a wearer-view associated with the first wearable computing device, and wherein the first wearable computing device is associated with a first user-account; (b) analyzing the gaze data from the first wearable computing device to detect one or more occurrences of one or more advertisements in the gaze data; (c) based at least in part on the one or more detected advertisement occurrences, determining an individual gaze value for the first user-account; and (d) sending a gaze-value indication to the first user-account, wherein the gaze-value indication indicates the individual gaze value for the first user-account.

In yet a further aspect, an exemplary computer-implemented method may involve: (a) receiving, at a wearable computing device, gaze data that is indicative of a wearer-view associated with the wearable computing device; (b) the wearable computing device analyzing the gaze data to detect one or more occurrences of one or more advertisement spaces in the gaze data; (c) based at least in part on the one or more detected advertisement-space occurrences, the wearable computing device determining an individual gaze value for a user-account that is associated with the wearable computing device; and (d) the wearable computing device displaying the individual gaze value.

In an additional aspect, an exemplary system may include a non-transitory computer-readable medium and program instructions stored on the non-transitory computer-readable medium. The program instructions may be executable by at least one processor to: (a) receive gaze data that is indicative of a wearer-view associated with the wearable computing device; (b) analyze the gaze data to detect one or more occurrences of one or more advertisement spaces in the gaze data; (c) based at least in part on the one or more detected advertisement-space occurrences, determine an individual gaze value for a user-account that is associated with the wearable computing device; and (d) display the individual gaze value.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 9 illustrates a schematic drawing of a wearable computing device according to an exemplary embodiment.

DETAILED DESCRIPTION

Figure 1:
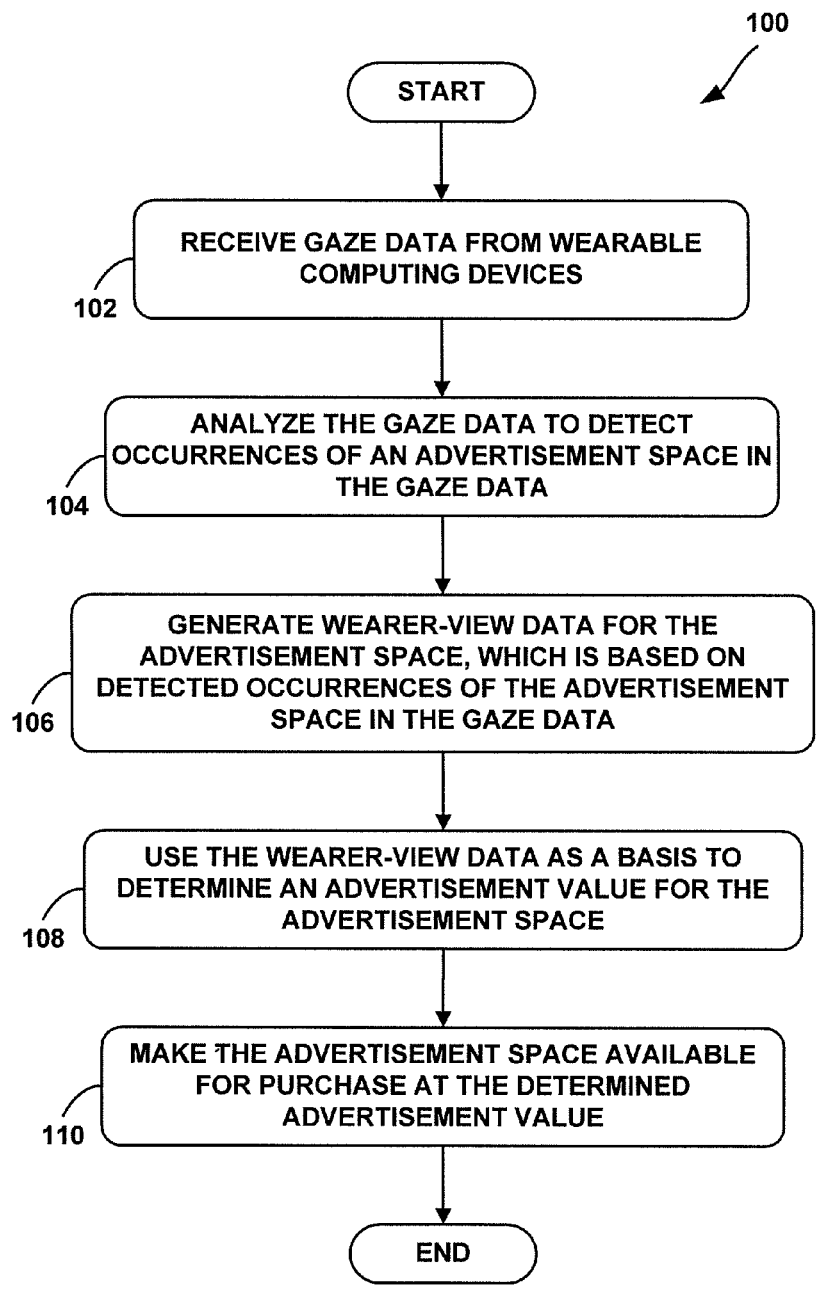
FIG. 1 is a flow chart illustrating a method according to an exemplary embodiment.

Exemplary methods and systems are described herein. It should be understood that the word "exemplary" is used herein to mean "serving as an example, instance, or illustration." Any embodiment or feature described herein as "exemplary" is not necessarily to be construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

I. Overview

A. Valuing Ad Space Based on Gaze Data

Many existing methodologies for valuing physical advertising space involve use of different types of data to estimate how many people view an advertisement space (referred to interchangeably as an "ad space") and/or how effective the advertisement space is at delivering the intended message to the viewer. These methodologies often rely on demographic information and other such indirect measurements of the potential audience for an ad space. Since these methodologies only estimate how many people actually view an ad space and/or who the people are that actually view the ad space, and do not incorporate actual viewership data, the results are often inaccurate.

Some existing valuation techniques do incorporate actual viewership data, which is typically collected for a test group and then extrapolated to the population as a whole (or to a larger group, such as a target market). However, gathering such viewership data with existing methodologies can often be time-consuming and difficult. For example, such techniques often involve polling people in a test group individually or laboriously observing how many people actually view an ad space (e.g., counting vehicles that pass by a billboard). Because of the effort required, advertising is typically limited to certain defined types of spaces (e.g., billboards, television commercials, websites, etc.) for which representative viewership data can be most-readily obtained.

Since most any physical space that is seen by people has some value for purposes of advertising, current valuation techniques do not allow for capitalization of many would-be advertising spaces. While the individual values of such spaces may be small, the cumulative value of all such spaces may be significant. However, due to the limitations of current advertisement valuation and marketing techniques, much of the potential value of such spaces has not been monetized.

Accordingly, exemplary methods and systems may help to determine the value of advertising spaces in a manner that may be more accurate, and may require less data-collection effort than existing advertisement-valuation techniques. In particular, exemplary methods may utilize "gaze data," from a number of wearable computers, which is indicative of what the wearers of the wearable computers are actually viewing, in order to value physical spaces.

For example, point-of-view (POV) videos from a number of wearable computers may be analyzed in order to determine how frequently a certain space is captured in the POV videos. Notably, POV video from wearable computers may provide a fairly accurate indication of what a user is actually looking at. Therefore, aggregating such POV videos from a number of users may help to more accurately value advertising rights to physical spaces. Additionally, the wearers of the wearable computing devices may elect to make their respective user-profiles available, such that individual characteristics of each wearer who views an advertisement space may be considered. This information may then be used to determine the value of the physical space.

Furthermore, a cloud-based server system may aggregate gaze data from many wearable computers, and use the gaze data to determine wearer-view data for various advertisement spaces. As such, an exemplary embodiment may provide advertisement valuation that is carried out automatically, without the effort required for manual data collection, and is more accurate, as the valuation is based on data that more-accurately captures what people are actually viewing.

B. Gaze Valuation for Individual Users

In a further aspect, an exemplary method may be implemented to determine what an individual user's gaze is worth. In particular, a user who is wearing a wearable computer with a head-mounted display (HMD) may send POV video from a camera attached to their HMD to an advertisement server system. Further, the user may opt in to a program where the POV video (and possibly other forms of gaze data) can be used for gaze valuation and/or to value ad spaces. Accordingly, the server system may analyze the gaze data to detect when the user views ad spaces. The individual gaze value for the user can then be determined based on the ad spaces that the user has viewed.

Further, in many instances, additional information, such as consumer data, demographic information, income, job title, hobbies, and/or interests, among others, may also be considered when determining a gaze value. For example, consider two users who view the exact same advertisements. In this scenario, the gaze value for one of these people might still be higher than for the other if, for example, one person has a significantly higher income than the other. Other examples are also possible.

Yet further, the historical efficacy of advertisements may be considered when determining a gaze value. For example, consider again two people who view the exact same advertisements. If, in the past, one user seems to have been influenced more by advertisements (e.g., as indicated by a pattern of purchasing products subsequent to viewing advertisements for the products), then this user's gaze value may be higher. Other examples are also possible.

To obtain their gaze value, a user may create a user-account and register a wearable computing device (and possibly other devices) to their user-account. As such, when the server receives gaze data from a given device, the server may associate the gaze data with the user-account to which the given device is registered. Then, each time the server detects an advertisement space in gaze data associated with a given user-account, the server may determine what the occurrence of the ad space is worth (e.g., what having the user view the ad space is worth to an advertiser). This value may be referred to as the "gaze-value contribution" for the occurrence of the ad space in the gaze data. As such, the server may determine the user's individual gaze value based on gaze-value contributions from a number of ad spaces that occur in the user's gaze data.

As a specific example, the individual gaze value may be calculated as a dollar amount per day. As such, the server may monitor a given user's gaze data for occurrences of ad spaces, determine a gaze-value contribution for each occurrence of an ad space that is detected during a one-day period, and then determine an individual gaze value by summing gaze-value contributions from the one-day period. Alternatively, the server may sum the gaze-value contributions for ad-space occurrences on a daily basis, and determine the individual gaze value by averaging the daily total over a number of days. Other variations are of course possible.

Providing users with individual gaze values may be useful in various scenarios. In one aspect, the ability to learn an individual gaze value may be used as an incentive for a user to opt in to a program where the user provides and authorizes use of their gaze data. In particular, when gaze data is used to value advertisement spaces, increasing the number of wearable computing devices from which gaze data is available will typically increase the number of ad spaces that can be valued and/or improve how accurately these ad spaces are valued. Accordingly, a user may be provided with access to individual gaze valuation functions only after the user has created a user-account, agreed to provide gaze data from their wearable computing device (and possibly from other devices that the user may optionally associate with their user account), and authorized their gaze data to be used for purposes of advertisement valuation. Since knowing what their individual gaze is worth may be interesting to many users, access to this functionality may be an incentive for such users to provide and authorize use of their gaze data.

Furthermore, in some embodiments, individual gaze value may be more than just a metric that interests users. Rather, individual gaze value functionality may be utilized to determine payments that are actually paid out users who provide gaze data. More specifically, since gaze data is typically indicative of what a user is actually viewing, an ad space marketplace may be established where advertisers pay for rights to ad spaces that are valued using gaze data, and a portion of the money paid by the advertisers is distributed to the users who provide the gaze data. In particular, when an occurrence of an ad space is detected in gaze data for a given user-account, the server system may update wearer-view data used for valuation of the ad space, and may also determine a value to the advertiser of the particular user viewing the ad space (e.g., a gaze-value contribution for the occurrence of the ad space in the user's gaze data). A portion of this value may then be credited to the user-account and/or paid out to the user.

As an example of one such application, an ad marketplace may be set up to pay users who provide gaze data a 5% commission on ad spaces they view. As such, users who allow their gaze data to be used for ad valuation may be paid 5% of their individual gaze value in exchange for use of their gaze data. Other examples are also possible.

Note that herein, when gaze data is said to be associated with a given user-account, it should generally be understood that this gaze data was sent by a device that is associated with the given user-account (e.g., a device that is registered with the user-account). Further, gaze data and/or other information that is associated with a user-account may also be said to be associated with a user since, functionally, associating gaze data or any other data with a user will generally be accomplished by associating the data with the user's user account.

In a further aspect, when a user creates a user-account for which a gaze value may be determined, a user-profile for the user-account may be created as well. The user-profile may include or provide access to various types of information, from various sources, which is related to the user. For simplicity, examples set forth herein may simply refer to a user-account as including the information included in the associated user-profile. However, this should not be read as requiring that a user-account include a user-profile. It is possible, in some embodiments, that a user-account may not have an associated user-profile.

II. Exemplary Method

FIG. 1 is a flow chart illustrating a method according to an exemplary embodiment. The method 100 shown in FIG. 1 may be implemented by a computing device, and in particular, by a server system, in order to determine a gaze value for a wearable computing device and/or for a user-profile associated with the wearable computing device. According to an exemplary embodiment, the gaze value is based on point-of-view gaze data received from a wearable computing device (which may be referred to interchangeably as a wearable computing device or a wearable computer). Further, a server system that implements an exemplary method may be referred to as a gaze-valuation system, as a gaze-valuation server, as an ad-valuation server, or simply as a server system or server.

As shown by block 102, method 100 involves a gaze-valuation server receiving gaze data for a first wearable computing device, which is associated with a first user-account. The server may analyze the gaze data from the first wearable computing device to detect occurrences of advertisement spaces in the gaze data, as shown by block 104. Then, based at least in part on the detected ad-space occurrences, the server may determine an individual gaze value for the first user-account, as shown by block 106. The server may then send a gaze-value indication, which indicates the individual gaze value, to the first user-account, as shown by block 108.

In an exemplary method 100, the gaze data received for a given wearable computing device is generally indicative of the wearer-view associated with the wearable computing device. For example, server may receive gaze data from a wearable computing device in the form of point-of-view (POV) video that is captured at the wearable computing device. As such, the POV video may be monitored in order to detect when advertisement spaces occur in the video.

In an exemplary method, such as method 100, gaze data may additionally or alternatively take forms other than point-of-view video. For example, the gaze data may take the form of point-of-view images captured by a forward- or outward-facing camera on a wearable computing device or another device. As a specific example, a given wearable computing device may periodically take a picture using a camera on an HMD that is generally aligned with the wearer's field of view. The wearable computing device may send these periodically-captured pictures to the server system for use in an exemplary method. Other examples are also possible.

Since the gaze data from a given wearable computing device is generally indicative of the wearer-view of the wearable computing device's wearer, the gaze data may be interpreted to be generally indicative of what the wearer of the device is actually looking at. For instance, the gaze data may be analyzed to determine information such as when a wearer is looking at a particular ad space and/or how long the wearer was looking at the particular ad space, among other information. Accordingly, the gaze data may be used to determine a gaze value for the wearer.

In an exemplary embodiment, the individual gaze value for a user (which may also be referred to as the gaze value) is indicative of the value of the user's gaze to advertisers. More specifically, the value of the user's gaze may represent the cumulative value to advertisers of the user viewing advertisements over time. As such, determining the individual gaze value may involve determining what each view is worth to an advertiser (e.g., what each occurrence of an ad space in gaze data associated with the given user is worth) and calculating a total value for all of the user's views.

Exemplary systems will now be described before further details of exemplary methods are set forth.

III. Exemplary Server Systems

Figure 2:
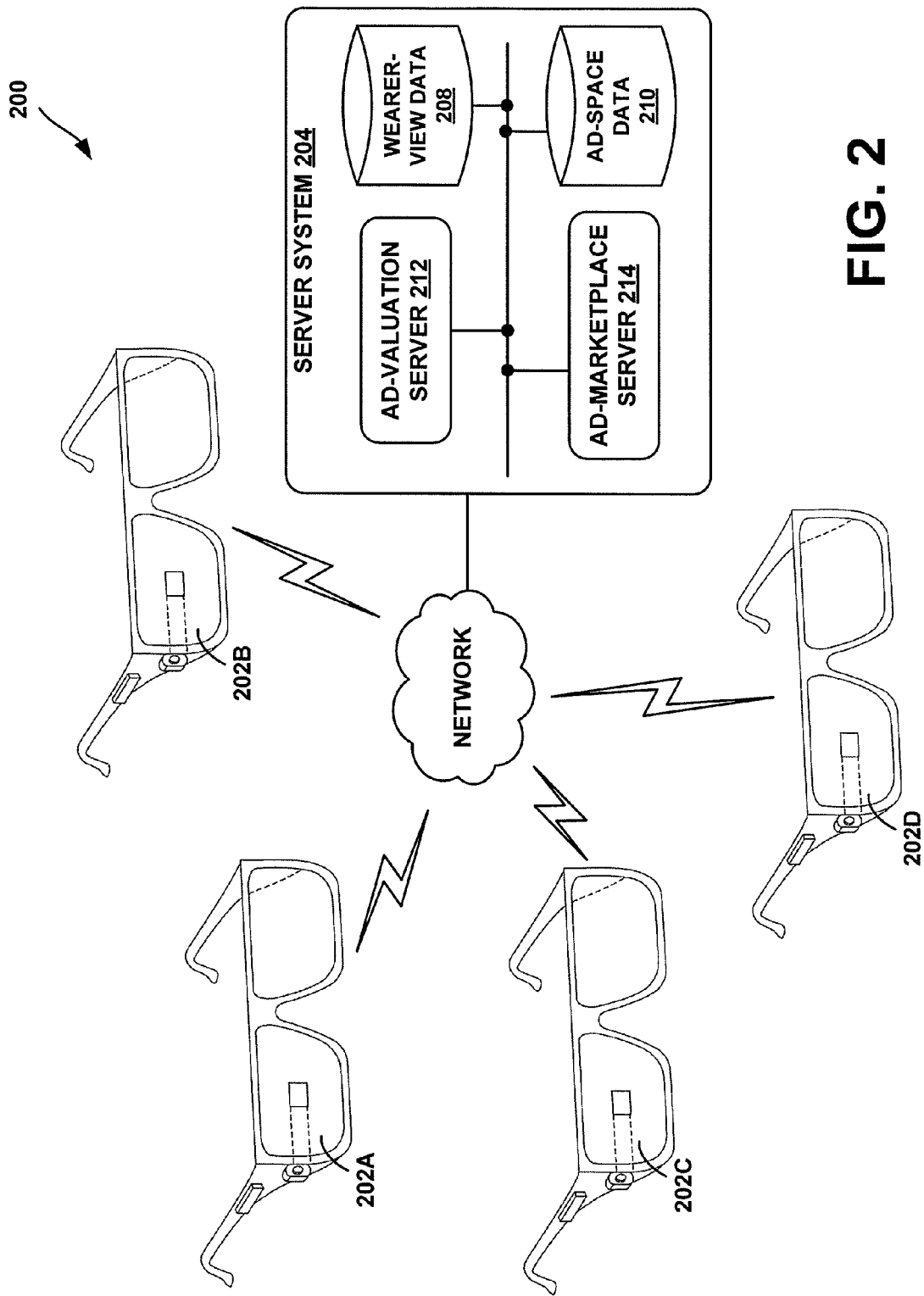
FIG. 2 is a simplified block diagram illustrating a communication network via which gaze data may be collected, according to an exemplary embodiment.

FIG. 2 is a simplified block diagram illustrating a communication network via which gaze data may be received, according to an exemplary embodiment. As shown, communication network 200 includes a number of wearable computing devices 202A to 202D, which are configured to communicate with a server system 204 via one or more networks 206.

In order to facilitate an exemplary method, the users of wearable computing devices 202A to 202D may register their respective devices and opt in to programs via which the users submit gaze data from their respective devices. As such, wearable computing devices 202A to 202D may send gaze data to the server system 204, which the server system may then use to determine respective gaze values for wearable computing devices 202A to 202D, possibly to valuate advertisement spaces as well.

In an exemplary embodiment, the server system 204 may be a computing system including one or more computing devices. In particular, server system 204 may be a cloud-based server system that is configured to receive gaze data, and to determine a gaze value for at least one of wearable computing devices 202A to 202D. In a further aspect, the server system 204 may also be configured to utilize the gaze data to value advertising spaces and/or support an advertisement-space marketplace for advertising spaces.

As noted, the gaze data in an exemplary embodiment may include point-of-view videos captured by a number of wearable computing devices. For example, some or all of the wearable computing devices 202A to 202D may include or take the form of glasses-style HMDs that each include a forward-facing video camera for taking point-of-view video (e.g., video that generally captures the perspective of a person wearing the HMD). As such, when the HMD is worn, the forward-facing camera will capture video and/or images that are generally indicative of what the wearer of the HMD sees. Note that exemplary glasses-style HMDs will be described in greater detail with reference to FIGS. 7A, 7B, 8A, 8B, and 9.

Further, server system 204 may include or be in communication with an ad-valuation server 212 and an ad-marketplace server 214. In some embodiments, ad-valuation server 212 and ad-marketplace server 214 may be separate server systems, which each include one or more computing devices. In other embodiments, some or all of the functionality attributed to ad-valuation server 212 and ad-marketplace server 214 may be provided by a single server system, which may include one or more computing devices.

In an exemplary embodiment, ad-valuation server 212 may be configured to receive gaze data from wearable computing devices 202A to 202D. Further, ad-valuation server 212 may analyze the received gaze data for occurrences of one or more ad spaces, and generate wearer-view data for the ad spaces based on occurrences of the ad spaces in the gaze data.

In a further aspect, the server system 204 may include or have access to a wearer-view database 208 that includes wearer-view data for a number of advertisement spaces (e.g., ad spaces indicated by ad-space database 210). When ad-valuation server 212 generates wearer-view data, ad-valuation server 212 may store the generated data in wearer-view database 208. Accordingly, server system 204 may access the wearer-view database 208 to retrieve wearer-view data for a given ad space, which in turn may be used to determine the ad value for the given ad space.

To assist the server in detecting occurrences of various ad spaces in gaze data, advertisement server 204 may include or have access to an ad-space database 210 that includes information that can be used to identify various ad spaces. Accordingly, ad server system 204 may use the identifying information from ad space database 210 to determine when ad spaces occur in gaze data from wearable computing devices 202A to 202D. Further, in embodiments that utilize location data for ad spaces, ad-space database 210 may also store location information for individual ad spaces.

In another aspect, ad-valuation server 212 and/or other components of system 204 may additionally or alternatively be configured to use gaze data to determine an individual gaze value for a given user-account. As such, ad-valuation server 212 and/or other components of system 204 may include program instructions stored in a tangible computer-readable medium that are executable to provide the functionality described herein, and possibly to provide other functionality as well.

In another aspect, server system 204 may include ad-marketplace server 214, which is configured to provide an advertisement marketplace via which advertisement spaces that are valued by ad-valuation server 212 can be bought and sold. Further, ad-marketplace server 214 may facilitate transactions between parties in such an advertisement marketplace. Data related to advertisement space in the advertisement marketplace may be stored in ad-space database 210.

IV. Detecting Advertisement Spaces in Gaze Data

As noted above, an exemplary method 100 may involve analysis of gaze data to detect when advertisement spaces occurs in the gaze data. To do so, an exemplary server system 200 may employ various types of video and/or image-processing techniques. For instance, advertisement server system 204 may implement various well known and yet-to-be-developed techniques for object recognition in video and/or still images in the process of recognizing advertising spaces.

In some cases, an ad space may be identified in gaze data by way of the advertisement that is displayed in the ad space. For example, ad-space database 210 may include data related to which specific advertisements are being displayed in which ad spaces (and may further indicate when there is no advertisement being displayed in a given ad space). As such, ad-valuation server 212 may search for advertisements that are currently being displayed in gaze data. To do so, the ad-valuation server may user various visual search techniques that are now known or yet to be developed in order to identify an advertisement in gaze data.

In other cases, an ad space may itself be identified, without necessarily relying on the particular ad that is being displayed in the ad space. (Note that this functionality may be particularly useful in cases where an ad space is empty.) In such an embodiment, detecting that an advertisement space occurs in gaze data may involve recognizing when the gaze data includes an object or a certain combination of objects that are associated with a particular advertisement space. For example, to recognize advertisement space on the bumper of a particular car, gaze data may be analyzed for an object shaped and/or having coloration that is characteristic of a car bumper. Further, the gaze data may be analyzed for an object having such a shape and/or coloration in conjunction with a license plate having a certain license plate number. In such an embodiment, the server system may consider an occurrence of a bumper in combination with the license plate number for the specific car to be an occurrence of the ad space on the car's bumper. Many other examples are also possible.

In some cases, searching gaze data from a large number of wearable computing devices for a large number ad spaces may be data intensive. Accordingly, an exemplary server and or wearable computing devices may implement pre-processing techniques to tag and ID certain types of objects or certain types of information in gaze data, which may help to speed up the process of detecting ad spaces. In some instances, wearable computing devices and/or the server may also store gaze data for processing when, e.g., a wearable computing device is offline, or when the amount of real-time data being collected is generally less. For example, a server may use certain processing resources to receive incoming gaze data during the day, when more gaze data may be received, and then re-assign these processing resources to analyze stored gaze data for ad spaces at night, when less new gaze data may be received.

In some embodiments, a server system may utilize location data to detect an occurrence of an ad space in gaze data. For example, a server system may determine or be provided with the geographic location of a particular ad space (e.g., the GPS coordinates of the ad space). Then, when the ad space is detected in gaze data from a particular wearable computing device, the server may determine the location of the wearable computing device. If this wearable computing device is located such that the ad space could be visible to the wearer of the wearable computing device (e.g., within a predetermined distance from the location of the ad space), then the server system may consider this an occurrence of the ad space. However, if the wearable computing device that provided the gaze data is located such that the ad space could not be viewed by the wearer (e.g., not within a predetermined distance from the location of the ad space), then the server system may not consider this an occurrence of the ad space.

As another example, a server system may use the geographic location of a particular ad space to limit the gaze data that is monitored for the ad space. For instance, the server may determine the locations of wearable computing devices from which gaze data is received. As such, the server may only monitor gaze data that is received from wearable computing devices that are located within a predetermined distance from the ad space. Other methods that utilize the location of an ad space when detecting occurrences of the ad space in gaze data are also possible.

In some embodiments, radio frequency identification (RFID) may be used to help detect occurrences of an ad space in gaze data. In particular, an ad space may be associated with a certain RFID tag, and wearable computing devices may be configured with RFID readers. As such, when a wearable computing device detects an RFID tag from an ad space, the wearable computing device may relay this to the server system. For instance, when the wearable computing device detects an RFID that is associated with an ad space, it may insert metadata into the gaze data which indicates the RFID tag and the time at which the RFID tag was detected. Alternatively, the wearable computing device may send a separate message indicating that the RFID tag was detected at a particular time. In either case, the server system can then search for the associated ad space in gaze data that is received from the wearable computing device at or near the time when the RFID tag is detected. This may help the server system to more efficiently detect occurrences of ad spaces, as the timing with which the RFID tags are detected may indicate, for example, times in corresponding point-of-view video where the ad space is likely to occur. Further, various types of RFID may be utilized, such as near-field communications (NFC) and/or other types of RFID, depending upon the implementation.

In some embodiments, barcodes may be used to help detect occurrences of an ad space in gaze data. For instance, a barcode that identifies an ad space may be displayed within or near to an ad space. The server system may then search for barcodes within gaze data. When a barcode associated with a particular ad space is detected, the server may consider this to be an occurrence of the ad space, or may treat this as a factor that, along with other factors, can indicate that there is an occurrence of the ad space in the gaze data. Various types of barcodes, such as high capacity color barcodes (HCCBs) and/or quick response (QR) codes may be utilized in such an embodiment. Other types of barcodes are possible as well.

It should be understood that the above techniques for detecting occurrences of ad spaces are not intended to be limiting. Other techniques are also possible.

V. Determining a Gaze Value

As noted in reference to block 106 of FIG. 1, an exemplary method 100 may involve a wearable computing device and/or a server system determining an individual gaze value for a given user-account, based on advertisements that are detected from a device or devices associated with the user-account. The gaze value may be determined using a number of different techniques, which may vary from implementation to implementation.

In a basic embodiment, the server system may value each view of an advertisement space equally, without regard to who is viewing the ad space, how long they view it, what ad (if any) is being displayed in the ad space, or the characteristics of the ad space itself. In this scenario, each occurrence of an ad space may be valued equally. Therefore, the server system may determine the gaze value for a given user-account by determining the total number of ad-space occurrences during the period over which a user's gaze value is being calculated, and multiplying the total number by a universally-defined value for a single view.

In other embodiments, the server system may determine an individual gaze-value contribution for each occurrence of an ad space. As such, the individual gaze-value contribution may vary from occurrence to occurrence, depending upon which user is viewing the ad space, how long the user views the ad space, characteristics of an ad that is being displayed in the ad space, characteristics of the ad space itself, and/or other factors.

A. Gaze Value Based on Per-Occurrence Gaze-Value Contributions

Figure 3A:
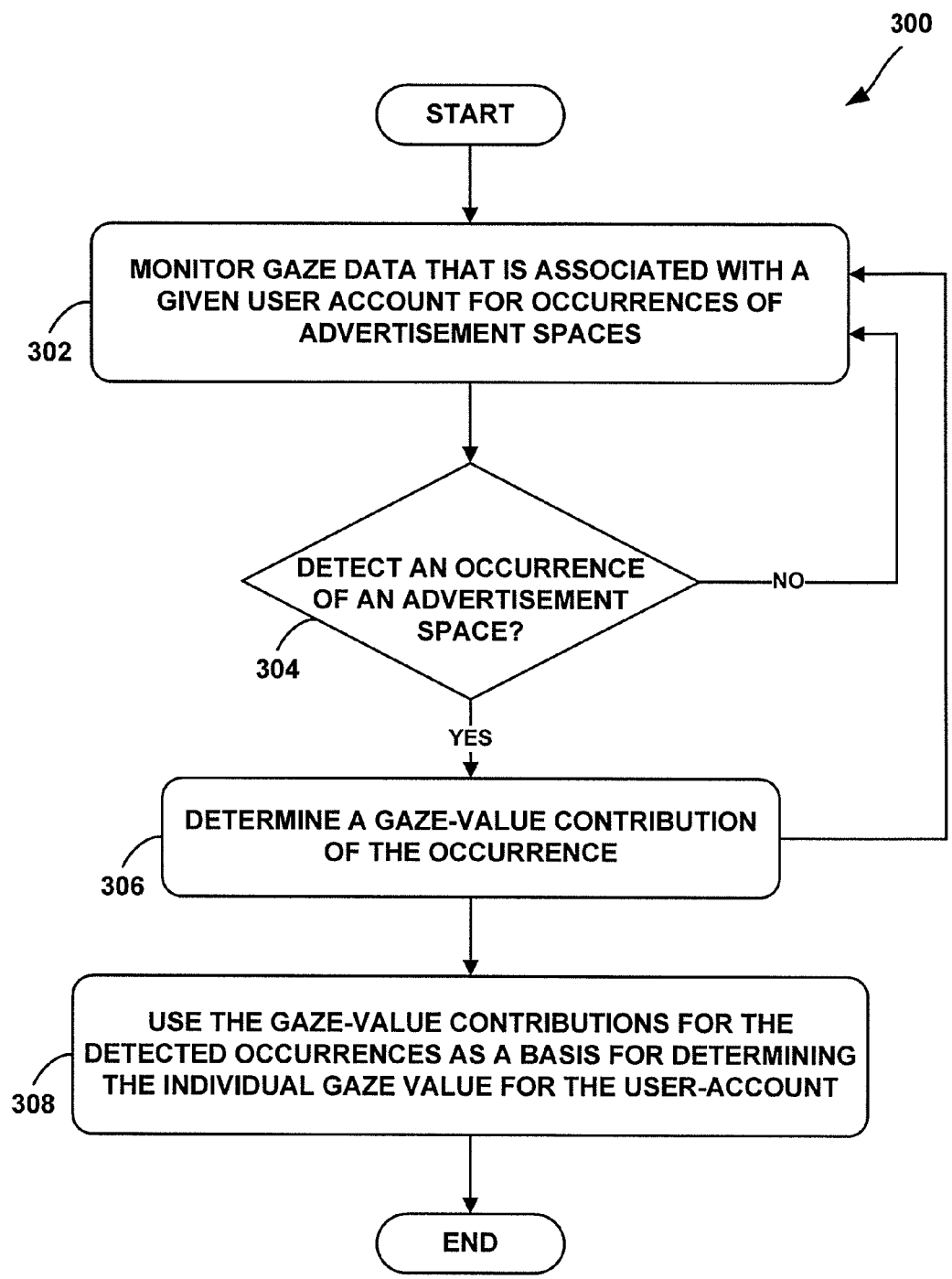
FIG. 3A is a flow chart illustrating a method for determining gaze value, according to an exemplary embodiment.

FIG. 3A is a flow chart illustrating a method for determining gaze value, according to an exemplary embodiment. In particular, FIG. 3A illustrates a method 300 in which the gaze value for a given user-account is based on individual gaze-value contributions of occurrences of the ad space in gaze data associated with the given user-account.

More specifically, method 300 involves monitoring gaze data that is associated with a given user account for occurrences of advertisement spaces, as shown by block 302. Each time an advertisement space is detected, as shown by block 304, the server system may determine a gaze-value contribution of the occurrence, as shown by block 306. The server system may further determine gaze-value contributions for a number of occurrences by repeating blocks 304 and 306 as additional ad-space occurrences are detected. The server system may then use the gaze-value contributions for the detected occurrences as a basis for determining the individual gaze value for the user-account, as shown by block 308.

In some embodiments, such as method 300 of FIG. 3A, the gaze-value contribution for each occurrence may be determined in real-time as each occurrence is detected. However, it should be understood that the gaze-value contribution for some or all occurrences of an ad space may be calculated at a later time, based on wearer-view data that is stored as the occurrences are detected in the gaze data.

A server may use various techniques to determine the individual gaze-value contribution for a given occurrence of an ad space in gaze data. Such techniques may utilize various different factors to determine the gaze-value contribution for a given occurrence. In some embodiments, the server may determine a weighting value for an occurrence, which may then be applied to a "standard" gaze-value contribution to determine the gaze-value contribution for the particular occurrence. In such an embodiment, the weighting value may be based on various factors or combinations of factors, such as the particular wearable computing device from which the gaze data including the particular occurrence was received, the duration of the occurrence, characteristics of the person who viewed (e.g., as indicated by the user-profile associated with the occurrence), the focus value of the occurrence, and/or other factors.

Once a server system has determined the individual gaze-value contributions for a number of occurrences, the server may use various techniques to determine the gaze value for the user. For example, in some embodiments, the server may determine the gaze value by summing the gaze-value contributions of some or all of the detected occurrences. As another example, in some embodiments, the server may determine the gaze value by averaging the gaze-value contributions of some or all of the detected occurrences. Other examples are also possible.

In some cases, the gaze-value contribution for each occurrence of an ad space may be a dollar amount that is attributed to the occurrence. As such, the server may determine a dollar amount for the gaze value by summing the gaze-value contributions. In other cases, the gaze-value contribution for each occurrence of the ad space may be a price rate (e.g., dollars per month, dollars per week, etc.) that is attributed to the occurrence of the ad space. As such, the server may determine the ad value by summing or averaging the gaze-value contributions to get a total or an average price rate, respectively. Other examples are also possible.

It should be understood that techniques described herein for determining an individual gaze value and/or determining gaze-value contributions of individual occurrences of an ad space are not intended to be limiting. Other techniques for determining an individual gaze value and/or determining gaze-value contributions of individual occurrences are also possible, without departing from the scope of the invention.

B. Gaze-Value Contribution Based on Duration

As noted, the server system may consider the duration of an occurrence when determining the portion of the ad value that is attributable to a given ad-space occurrence associated with a given user-account. In some embodiments, a predetermined rate may be defined for gaze valuation (e.g., dollars per minute), and this rate may be used in conjunction with the duration of an occurrence to determine the gaze-value contribution of the occurrence (e.g., by multiplying the rate by the duration).

In other embodiments, the server system may determine a total view time for an ad space by summing the respective durations of all occurrences associated with a number of different user-accounts (e.g., all user-accounts that have authorized collection and use of gaze data for such a purpose). In some cases, the server system may extrapolate from the gaze data to estimate a total view time for all views of an ad space (whether captured in gaze data or not). In either case, the ad-value portion that is attributable to the given occurrence may be based on the ratio of the duration of the occurrence to the total view time. For instance, if an ad space is valued at a rate of $12 per day, and the server estimates that an ad space averages two hours of viewing per day, a $0.10 portion may be attributed to an occurrence lasting for one minute. Other examples are also possible.

In a further aspect, when a gaze-value contribution of an occurrence accounts for the duration of the occurrence, it may also take into account a diminishing return of viewing duration. For example, if a person views an advertisement for one minute, the first twenty seconds that a person views the advertisement may be considered more valuable than the next twenty seconds during which the person continues to view the advertisement, which in turn may be considered more valuable than the final twenty seconds in the minute-long view. Similarly, having a user view one advertisement may be considered less valuable overall than either the same user view five advertisements for one minute each or five different users viewing the same or different advertisements for one minute each. As such, when duration is considered the diminishing returns of extended viewing periods may be taken into account.

C. Gaze-Value Contribution Based on Focus Value for an Occurrence

While detecting an ad space in gaze data from a wearable computing device may generally indicate that the ad space was within the field of view of the wearer, it is possible that the ad space was in the periphery of the wearer's field of view, was in the center of the wearer's field of view, or somewhere in between. Furthermore, the wearer can move their eyes such that they are focusing on the ad space or such that they are focusing elsewhere in their field of view. Accordingly, in some applications, an exemplary method may vary the gaze-value contribution for a given occurrence based on the amount of attention paid to the ad space during the occurrence. Generally, the higher the focus value for a given occurrence, the higher the gaze-value contribution of a given occurrence. However, there may be exceptions to this general principal, without departing from the scope of the invention.

An exemplary server system may use various techniques to calculate a focus value for a given occurrence of an ad space in gaze data. In some implementations, the focus value may be a numeric value that increases as more attention is paid to an ad space. However, in alternative implementations, it is possible that the focus value may be inversely proportional to the amount of attention paid to the ad space.

In some embodiments the focus value may be based at least in part on a location of the ad space in the gaze data. For example, consider an embodiment where the gaze data from a given wearable computing device includes POV video from the device. The server system may determine the location of the advertisement space in the point-of-view video, and then use the location of the advertisement space in the point-of-view video as a basis to determine the focus value. For instance, the server system may determine coordinates of the ad space (e.g., the coordinates of the center of the ad space) within one or more video frames. The server may then use the determined coordinates as input when determining a focus value for the detected occurrence. In particular, the closer the location of the advertisement space is to the center of the video frame, the greater the determined focus value, and vice versa. Thus, in practice, the server may increase the focus value as the distance between the location of the ad space and the center of the video frame decreases.

Note that if multiple frames with the object are used to calculate the location of the ad space, the server system may determine the coordinates of the object in each frame and then average the coordinates from the frames to determine the location of the object in the video frame. In some embodiments, the server may implement Visual Simultaneous Localization and Mapping (V-SLAM) to track the location of an object from frame to frame. V-SLAM can provide a registered 3D point cloud of the world, which identifies the general shape of objects and the respective distances to the objects, and allows for pixels in one frame to be related to pixels in another frame. V-SLAM is well known in the art and therefore is not discusses in further detail herein. Furthermore, it should be understood that other techniques may also be utilized instead of or in addition to V-SLAM.

In some embodiments, the server may utilize eye-tracking data corresponding to the occurrence of the ad space when determining a focus value for the occurrence. The eye tracking data may generally be indicative of a direction that the wearer is looking Accordingly, the server may determine the location of the advertisement space in the point-of-view video, and then use eye-tracking data from the wearable computing device that provided the gaze data to determine a wearer-gaze location in the point-of-view video at or near the time when the ad space occurs in the video. The server may then determine the proximity of the wearer-gaze location to the location of the advertisement space in the point-of-view video, and use the proximity as a basis for determining the focus value for the particular occurrence of the advertisement space. In an exemplary embodiment, the server may generally increase the focus value as the distance between the ad-space location and the wearer-gaze location decreases.

In some embodiments, the server may use movement of the ad space during a given occurrence in POV video as a basis for determining the focus value for the occurrence. For instance, if an ad space is detected in a number of consecutive video frames, the server may determine the location of the ad space in each of the frames (or possibly in a representative subset of the frames in which the ad space is detected). The server may then compare the determined locations of the ad space to determine how much the ad space moved during the occurrence of the ad space. If the ad space is relatively still and does not move significantly within the frame, this may be indication that the wearer focusing on the ad space. On the other hand, more movement of the ad space may indicate that the wearer is focusing on something other than the ad space. Accordingly, the server may generally increase the focus value of the occurrence as the amount of movement during the occurrence decreases, and vice versa.

In some embodiments, the server may use the amount of the point-of-view video frame that is occupied in POV video as a basis for determining the focus value for the occurrence. In particular, if the ad space occupies a large amount of the video frame, this may be an indication that the ad space is more prominent in the wearer's field of view and/or that the user is closer to the ad space. As such, if the ad space occupies a large amount of the video frame, the server may interpret this as an indication that the user is paying more attention to the ad space. Accordingly, the server may generally increase the focus value as the percentage of the video frame that is occupied by the ad space increases.

It should be understood that the focus value may be based on just one of the above factors or another factor altogether. Further, the focus value may also be based on a combination of some or all of the above factors and/or other factors.

D. Gaze-Value Contribution Based on User-Characteristics.

In some embodiments, an exemplary method may help account for the fact that views of an ad space by certain people may be considered more valuable than views of the same ad space by other people. As such, various types of information provided by and/or related to a given user-account may be used to determine a gaze-value contribution for an ad-space occurrence in gaze data for the given user-account.

For instance, a user-account may include or provide access to: (a) consumer information such as spending habits, locations of purchases, amounts of purchases, types or categories of purchases, timing of purchases, etc., (b) demographic information such as age or age group, ethnicity, nationality, sex, location of residence, and/or location of workplace, (c) contact and/or social networking information such as a user's contacts, and possibly data indicating a purchasing influence of the user with regard to their contacts (e.g., data indicating any correlation of the user's purchasing history to the wearers' friends' purchasing histories), and/or (d) other information such as income, job or job type, other job details, hobbies, interests, and so on. When a user has given permission for information from their user-account to be used for purposes of determining their individual gaze value, the server system may use such information to determine the gaze-value contribution that is attributable to a given occurrence of an ad space in gaze data associated with the user's account.

To provide one specific example, the server may determine an income level for a given user-account and then increase or decrease the gaze-value contribution for occurrences in the user's gaze data according to their income level. For example, number of income ranges may be mapped to certain adjustments that should be applied when determining gaze-value contribution. The adjustments may generally increase the gaze-value contribution for higher income ranges, and decrease the gaze-value contribution for higher income ranges.

In another application, the server may determine an average income level for a relevant group (e.g., users who have viewed the advertisement, a target user group for the ad displayed in the ad space, the population as a whole, etc.). The server may then adjust gaze-value contribution for an occurrence in gaze data associated with the user based on the relationship between the user's income level and the average income level (e.g., whether and/or by how much the user's income level is above or below the average income level). Other examples are also possible.

Furthermore, in some applications, the gaze-value contribution for an occurrence may not increase or decrease in proportion to associated user's income level. For example, a given advertisement may be targeted at a specified income range. As such, views by users that do not fall within the specified income range may be considered less valuable. Therefore, gaze-value contributions for user-accounts having an income level outside the income range may be reduced, regardless of whether the income level is above or below specified income range. Other examples are also possible.

As another specific example, the server may base the gaze-value contribution on how well demographic information from a user-profile matches a targeted demographic profile for the advertisement displayed in a detected ad space. The targeted demographic profile may indicate a single type of demographic information to be evaluated (e.g., male or female) or a combination of various types of demographic information (e.g., males between 30 and 45 years of age who live in an urban location). Other examples are also possible.

E. Gaze-Value Contribution Based on Context

In a further aspect, an exemplary method may help account for the fact that in some cases, a certain user viewing a certain advertisement in one context, may be considered more valuable than the same user viewing the same advertisement in another context. Accordingly, the gaze-value contribution for a given advertisement space that is detected in a user's gaze data may vary based on the advertisement that is displayed and context associated with detecting the advertisement space.

For instance, consider a user-profile that indicates the particular user is a scientist who is interested in the latest research in their field. Therefore, it may be determined that this user will likely be interested in an advertisement for an upcoming conference in their field. As such, gaze-value contributions of certain advertisements may be adjusted depending on whether or not the context in which the advertisement is viewed makes it more or less likely that this user will be interested in the advertisement and/or be prompted to act when they view the advertisement.

As a specific example, consider a scenario where the above-described user is driving to work at their laboratory, and sees a billboard while driving. In this scenario, context signals such as the day of the week, time, and/or the user's location may be used to determine that the user is "driving to work at their lab" (e.g., based on context signals indicating that the user is located on a highway on the laboratory, on a weekday, at 8:00 am). If the advertisement for upcoming conference in the user's field is displayed on the billboard in this context, it may be inferred that the user is likely to have work on their mind, and thus be more likely to be interested in and/or to act on this advertisement. However, if this same advertisement is displayed to the same user when the user is on vacation, context may be used to reduce the gaze-value contribution of this user viewing the advertisement.

In a further aspect, gave-value contribution in a given context may vary between different users (e.g., between different user-accounts). For example, in some cases, the gaze-value contribution corresponding to a first user viewing a certain advertisement in a certain context may be greater than the gaze-value contribution for another user viewing the same advertisement in same context. In particular, the relationship between characteristics of a user indicated by their user-account and a given context may be evaluated to determine whether an adjustment to a gaze-value contribution is appropriate in the given context.

For example, consider a first user and a second user who are both at a department store. An exemplary system and/or the users' respective devices may evaluate various context signals, such as each user's location (e.g., at the location of the department store), the time of day (e.g., a time during the business hours of the department store), and so on, to determine that the first user's context is "at the department store." However, employment information in the first user's user-account may indicate that the first user is an employee of the department store, while employment information (and other types of information) in the second user's user-account may reveal no such connection to the department store.

Note also that in some instances, context signals may be used to infer characteristics of a given user, such that use of information from a user-account may not be necessary. For instance, in the above example, it might be inferred that the first user is an employee of the department store from context signals that indicate, e.g., that the first user is typically located in the department store for eight hours per day, five days per week, during store business hours. Other examples are also possible.

Based on these relationships between the context and the information from the respective user characteristics of these users, the gaze-value contribution for the first user viewing a particular advertisement while located in the department store may be lower than the gaze-value contribution for the second user viewing the same advertisement while located in the department store. More specifically, the gaze-value contribution for the first user may be lower because the first user is an employee and thus may be considered unlikely to act on an advertisement while on the job, whereas the second user may be inferred to be shopper at the department store, since available information does not indicate to the contrary. This may be the case even if most or all other information regarding the two users is the same (e.g., the same or similar demographic information, same income range, etc.).

To determine a context associated with a given advertisement being detected in gaze data for a given user-account, a cloud-based server may be configured to use context data from a single device that is associated with the user-profile. For instance, referring back to FIG. 2, server system 204 may use context data from a single device, such as wearable computing device 202A, to determine context for the user-account that is associated with that device. Alternatively, the server may be configured to aggregate context data from two or more devices that are associated with the user-account, and use the aggregate context data to determine context for the user-account. For example, if a number of devices are all associated with the same user-account, such as wearable computing device 202A, a mobile phone, and a laptop computer, for example, then context data provided by some or all of the associated devices may be aggregated when determining context for the associated user-profile.

In an exemplary embodiment, the context associated with a given user-profile may be determined using various techniques. In general, a "context" may be determined based on various "context signals" or combinations of context signals. A context signal may be any signal that provides a measurement or otherwise provides information pertaining to the state or the environment associated with a certain subject (e.g., with a certain user, device, event, etc.). In this case, the context signals associated are generally pertain to a user-profile for a wearer of a wearable computing device. As such, the context signals may generally provide some type of information pertaining to the state or the environment of the wearer.

In some instances, a context may be a state associated with a particular context signals or set of context signals. However, a context may also be abstracted from the context signals upon which it is based. As such, a "context" may also be a data-based description or characterization of an environment or state that is determined or derived from one or more context-signals. For example, contexts may take the form of data indicating environment or state information such as "at home," "at work," "in a car," "indoors," "outside," "in a meeting," etc. Furthermore, a context may be a qualitative or quantitative indication that is determined based on one or more context signals. For example, context signals indicating that that it is 6:30 AM on a weekday and that a user is located at their home may be used to determine the context that the user is "getting ready for work."

Many types of information, from many different sources, may be used as context signals or provide information from which context signals may be derived. For example, context signals may include: (a) the current time, (b) the current date, (c) the current day of the week, (d) the current month, (e) the current season, (f) a time of a future event or future user-context, (g) a date of a future event or future user-context, (h) a day of the week of a future event or future context, (i) a month of a future event or future user-context, (j) a season of a future event or future user-context, (k) a time of a past event or past user-context, (l) a date of a past event or past user-context, (m) a day of the week of a past event or past user-context, (n) a month of a past event or past user-context, (o) a season of a past event or past user-context, ambient temperature near the user (or near a monitoring device associated with a user), (p) a current, future, and/or past weather forecast at or near a user's current location, (q) a current, future, and/or past weather forecast at or near a location of a planned event in which a user and/or a user's friends plan to participate, (r) a current, future, and/or past weather forecast at or near a location of a previous event in which a user and/or a user's friends participated, (s) information on user's calendar, such as information regarding events or statuses of a user or a user's friends, (t) information accessible via a user's social networking account, such as information relating a user's status, statuses of a user's friends in a social network group, and/or communications between the user and the users friends, (u) noise level or any recognizable sounds detected by a monitoring device, (v) items that are currently detected by a monitoring device, (w) items that have been detected in the past by the monitoring device, (x) items that other devices associated with a monitoring device (e.g., a "trusted" monitoring device) are currently monitoring or have monitored in the past, (y) information derived from cross-referencing any two or more of: information on a user's calendar, information available via a user's social networking account, and/or other context signals or sources of context information, (z) health statistics or characterizations of a user's current health (e.g., whether a user has a fever or whether a user just woke up from being asleep), and (aa) a user's recent context as determined from sensors on or near the user and/or other sources of context information, (bb) a current location, (cc) a past location, and (dd) a future location, among others. Those skilled in the art will understand that the above list of possible context signals and sources of context information is not intended to be limiting, and that other context signals and/or sources of context information are possible in addition, or in the alternative, to those listed above.

In some embodiments, the detection or observation of a certain event in data from a certain data source may itself be interpreted as a context signal. For example, the fact that a certain word is detected in an audio signal from a microphone may be interpreted as a context signal providing context to the event of that word being spoken. Other examples are also possible.

In some embodiments, context signals may be obtained or derived from sources such as a user's computer-based calendar, blog, webpage, social network account, and/or e-mail account, among others. For instance, context signals may be provided by user's calendar entries, e-mail messages, and social-network profile, messages, posts, and/or tweets. Further, in some embodiments, similar context signals may be obtained or derived from other users' computer-based calendars, blogs, webpages, social network accounts, and/or e-mail accounts, who are listed in a user's electronic contact list, listed as a "friend" in a user's social network, or otherwise associated with the user (provided such users have opted in to share such context information).

It should be understood that the above examples of contexts, context signals, techniques for determining a context, and/or techniques for using context when selecting an advertisement are provided for illustrative purposes, and are not intended to be limiting. Other examples and/or techniques are also possible.

F. Combining Various Factors to Determine a Gaze Value

Figure 3B:
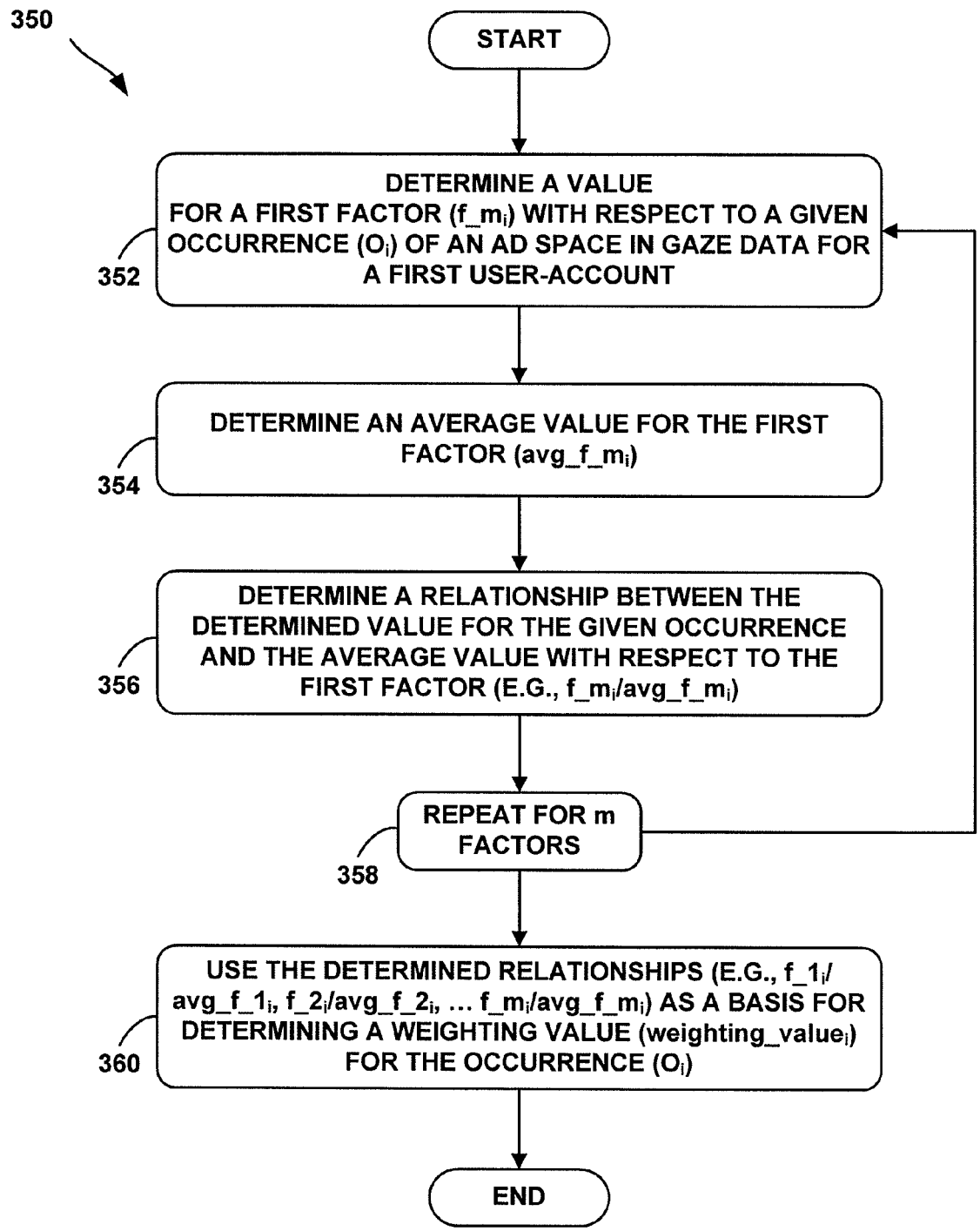
FIG. 3B is a flow chart illustrating a method for using multiple factors to determine an individual gaze value for a user-account, according to an exemplary embodiment.

FIG. 3B is a flow chart illustrating a method for using multiple factors to determine an individual gaze value for a user-account, according to an exemplary embodiment. In method 350 of FIG. 3B, a pre-determined base contribution for an ad space is weighted according to multiple factors in order to determine a gaze-value contribution for each occurrence of an ad space in gaze data for a given user-account. The individual gaze value for the user-account may then be determined from the collective knowledge provided by the gaze-value contributions of the ad-space occurrences detected in gaze data associated with the user-account.

Method 350 is described by way of example as being implemented by a server system, but could also be implemented by a wearable computing device, by another device or system, or by a combination of devices and systems.

Method 350 involves the server system determining a weighting value (weighting_value$_i$) to be applied for an occurrence of an ad space (O$_i$) in gaze data from a given user account, based on m different factors (f_1$_i$ to f_m$_i$). In particular, the server system may determine a value for a first factor (f_1$_i$) with respect to a given occurrence of an ad space in gaze data for a first user-account, as shown by block 352. The server system may then determine an average value for the first factor (avg_f_1$_i$), as shown by block 354. As such, the server system may determine a relationship between the determined value for the given occurrence and the average value with respect to the first factor (e.g., f_1$_i$/avg_f_1$_i$), as shown by block 356. If there are additional factors to consider (e.g., if m is greater than one), as indicated by block 358, then the server may repeat blocks 352 to 356 for the additional factors, until the relationship between the given user-account and relationship between the value for the given occurrence and the average value has been determined for each factor. Once all the factors have been evaluated, the server system may use the determined relationships as a basis for determining a weighting value for the occurrence, as shown by block 360.

Thus, for a given occurrence O$_i$, and values for a set of n factors f_1 to f_n, method 350 may be implemented to determine a weighting value, as a function of the respective relationships between the values of factors for the given occurrence f_1$_i$ to f_m$_i$ and the average value for factors avg_f_1$_i$ to avg_f_m$_i$. For example, weighting_value$_i$ may be calculated as:

$$\text{weighting\_value}_i = F[(f\_1_i/\text{avg}\_f\_1_i), (f\_2_i/\text{avg}\_f\_2_i), \ldots (f\_m_i/\text{avg}\_f\_m_i)]$$

Note that the particular function used may vary from implementation to implementation, depending upon the design goals.

Once the server has determined the weighting value, for a given occurrence O$_i$ of an ad space, the server may use a base contribution for the ad space in the ad space detected in occurrence O$_i$ to calculate the gaze value contribution for the occurrence as:

$$\text{gaze\_value\_contribution}_i = \text{base\_contribution}_i * \text{weighting\_value}_i$$

Further, the server system may repeat the above process to determine a gaze-value contribution for n occurrences O$_i$ in the gaze data for the user-account. As such, the individual gaze value for the user-account may be determined as a function of gaze_value_contribution$_i$ for i equal 1 to n. For example, the individual gaze value may be calculated as the sum of gaze_value_contribution$_i$ to gaze_value_contribution$_n$. Other examples are also possible.

It should be understood that many other types of information provided by and/or related to a given user-account may be considered, alone or in combination, when determining the gaze-value contribution of an ad space in gaze data for the given user-account. Further, information provided by and/or related to a given user-account may be considered in combination with other factors, such as duration of an occurrence and/or a focus value associated with the occurrence, when determining the gaze-value contribution for an occurrence.

G. Fitting Gaze-Value Contributions to Predetermined Ad Values

In some of the described embodiments, the gaze-value contribution for a given occurrence of an ad space may be calculated as the portion of a known ad value for the ad space that is attributable to the given occurrence.

Figure 4:
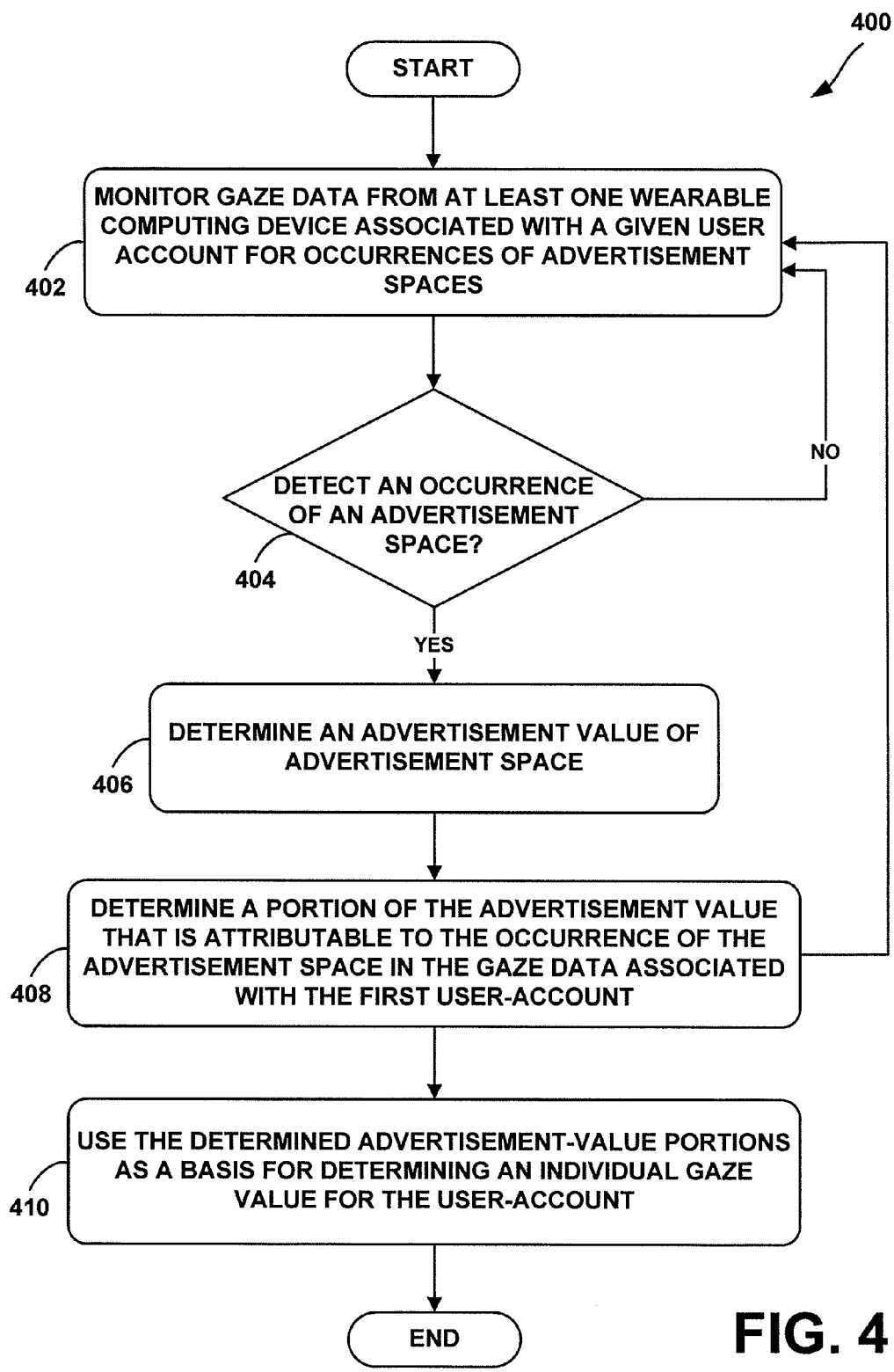
FIG. 4 is a flow chart illustrating a method for determining gaze value, according to an exemplary embodiment.

FIG. 4 is a flow chart illustrating a method for determining gaze value, according to an exemplary embodiment. In particular, FIG. 4 illustrates a method 400 in which the gaze-value contribution for each occurrence of an ad space is a portion of the ad value that is attributable to the particular occurrence.

More specifically, method 400 involves monitoring gaze data from at least one wearable computing device associated with a given user account (and possibly other devices associated with the same user-account) for occurrences of advertisement spaces, as shown by block 402. Each time an occurrence of an advertisement space is detected, as shown by block 404, the server system may determine an advertisement value of the advertising space, as shown by block 406. Further, the server system may determine a portion of the advertisement value that is attributable to the occurrence of the advertisement space in the gaze data associated with the first user-account, as shown by block 408. The first server system may repeat block 404 to 408 for a number of occurrences of advertisement spaces to determine portions of the respective advertisement values that are attributable to the respective occurrences number of ad-space occurrences. Accordingly, the server system may use the determined advertisement-value portions as a basis for determining an individual gaze value for the given user-account, as shown by block 410.

In an exemplary method 400, the function of determining the advertisement value of a given advertising space may be accomplished using various techniques. In some instances, there may be a built-in assumption that the ad value for a given ad space is equal to whatever is being paid for the ad space by the advertiser. Accordingly, the server system may simply determine a price that was paid for the ad space by an advertiser. For example, the server system may determine a fixed price that was paid for the ad space, or may determine a price rate (e.g., dollars per month, dollars per view, etc.).

However, in some cases, it may not be assumed that the ad value for an ad space is equal what the advertiser paid; or in other words, some embodiments may allow for the possibility of an advertiser "getting more than what they paid for." For example, if each view by a certain type of person (e.g., the target market) is considered to be worth a certain amount to an advertiser, the advertiser may pay an amount based on the expected number of views by the target market. However, if an ad space receives more than the expected number of views from the target market, then from the advertiser's perspective, the ad space is worth more than they paid for it. Furthermore, there may be cases where an ad space has been valued or could be valued, but has not been purchased by an advertiser.

Accordingly, the server system may additionally or alternatively use a measure of advertisement value other than what was actually paid for the advertisement space. For example, the server system may query an advertisement-value database, which indicates advertisement values that are based on detected occurrences of the advertisement space in gaze data from a plurality of wearable computing devices (and possibly gaze data from other types of devices as well). Methods for determining an ad value for and ad space based on gaze data from a number of wearable computing devices are described in greater detail with reference to FIGS. 5A to 7.

Further, in some embodiments, individual gaze valuation may be implemented in conjunction with an ad marketplace where advertisement spaces are generally valued based on gaze data. In such an embodiment, the server system may also use as the ad value, the price at which an ad space is being offered for sale in the ad marketplace.

It should be understood that techniques described herein for determining an ad value for a given ad space are not intended to be limiting. Other techniques for determining an ad value based on the ad-value contributions of individual occurrences are also possible, without departing from the scope of the invention. Further, it should be understood that the technique and/or format of the ad value may vary from one occurrence to another within the gaze data associated with a given account. For example, the server system may might use the actual purchase price for an ad space, when the purchase price is available, but use the ad value based on gaze data when a purchase price is not available or is otherwise deemed to be less accurate (e.g., when the purchase price is considered out of date).

In an exemplary method 400, the function of determining the portion of the advertisement value that is attributable to a given occurrence of a given advertisement space may be accomplished using various techniques.

In some embodiments, the server system may attribute an equal portion of the advertisement value to each occurrence of a particular ad space. For example, the portion of an ad space's value that is attributed to a given occurrence may be calculated by dividing the advertisement value by a total number of occurrences detected in gaze data from a number of devices associated with a number of different user-accounts. For instance, if an advertisement space is valued at $100 per month and the advertisement space averages ten occurrences per month in all available gaze data, a $10 portion may be attributed to a given occurrence of the ad space.

In some cases, the portion of an ad space's value that is attributed to a given occurrence may be based on an estimated number of total views of the ad space. In particular, the server system may extrapolate from the occurrences that are detected to determine an estimated number of total views. This estimation may account for all views of an ad space, regardless of whether the view was captured in gaze data. This may be useful as there may be many cases where those that view an ad space are not wearing a wearable computer that is configured to capture and/or provide gaze data. As one specific example, consider the case where it is assumed that one out of every thousand views will be captured in gaze data. In this case, if an advertisement space is valued at $100 per month and the advertisement space averages ten occurrences per month in all available gaze data, the server system may calculate that there are 10,000 views per month. Accordingly, a $0.01 portion may be attributed to a given occurrence of the ad space. Other examples are also possible.

In some embodiments, an exemplary method may help account for the fact that views of an ad space by certain people may be considered more valuable than views of the same ad space by other people. As such, various types of information provided by and/or related to a given user-account may be used to determine an ad-value portion that is attributable an occurrence of an ad space in gaze data associated with the given user-account. For instance, a user-account may include or provide access to: (a) consumer information such as spending habits, locations of purchases, amounts of purchases, types or categories of purchases, timing of purchases, etc., (b) demographic information such as age or age group, ethnicity, nationality, sex, location of residence, and/or location of workplace, (c) contact and/or social networking information such as a user's contacts, and possibly data indicating a purchasing influence of the user with regard to their contacts (e.g., data indicating any correlation of the user's purchasing history to the wearers' friends' purchasing histories), and/or (d) other information such as income, job or job type, other job details, hobbies, interests, and so on. When a user has given permission for information from their user-account to be used for purposes of determining their individual gaze value, the server system may use such information to determine an ad-value portion that is attributable to a given occurrence of an ad space in gaze data associated with the user's account.

It should be understood that many other types of information provided by and/or related to a given user-account may be considered, alone or in combination, when determining the portion of the ad value to attribute to an occurrence of an ad space in gaze data for the given user-account. Further, information provided by and/or related to a given user-account may be considered in combination with other factors, such as duration of an occurrence and/or a focus value associated with the occurrence, when determining the portion of the ad value to attribute to the occurrence.

H. Gaze-Value Contributions on Per-Ad Basis

In the above examples, the gaze value is based upon ad-value portions that are determined on a per-occurrence basis. However, in some embodiments, the gaze value may only consider each ad space once when determining a gaze value for a given user-account. As such, the server system may effectively ignore subsequent occurrences of the same ad space in gaze data associated with a given user-account. For example, the server system may determine that a given ad space has occurred in gaze data for a certain number of user-accounts. The server system may then divide the ad value for the ad space by this number to determine the portion that is attributable to one user-account. As another example, the server may extrapolate from the total number of user-accounts have provided gaze data including an occurrence of a given ad space to determine an estimated number of users that have viewed (or will view) the ad space, and divide the ad value by the estimated number of users who have viewed the ad space, in order to determine the portion of the ad value that is attributable to one user-account. Other examples are also possible.

VI. Sending a Gaze-Value Indication

Referring back to method 100 of FIG. 1, once a gaze value for a given user-account has been determined, the server may send a gaze-value indication to the given user-account, which indicates the individual gaze value that was determined. This may be accomplished in various ways. For example, the server system may (a) send an e-mail message to at least one e-mail account associated with the first user-profile, (b) send a text or multimedia message to at least one phone number associated with the first user-profile, (c) initiate an automated phone call to at least one phone number associated with the first user-profile, and/or (d) display the determined gaze value in a web browser or another application via which the user has accessed their user-account. Other techniques for providing a user with their individual gaze value are also possible.

VII. Determining the Value of an Advertisement Space

As noted, in some embodiments, an exemplary system may also be configured to use gaze data to determine advertisement values for ad spaces, in addition to using the gaze data to determine individual gaze values for users. In such an embodiment, an exemplary system may be configured to determine an advertisement value for almost any time of physical space.

Figure 5A:
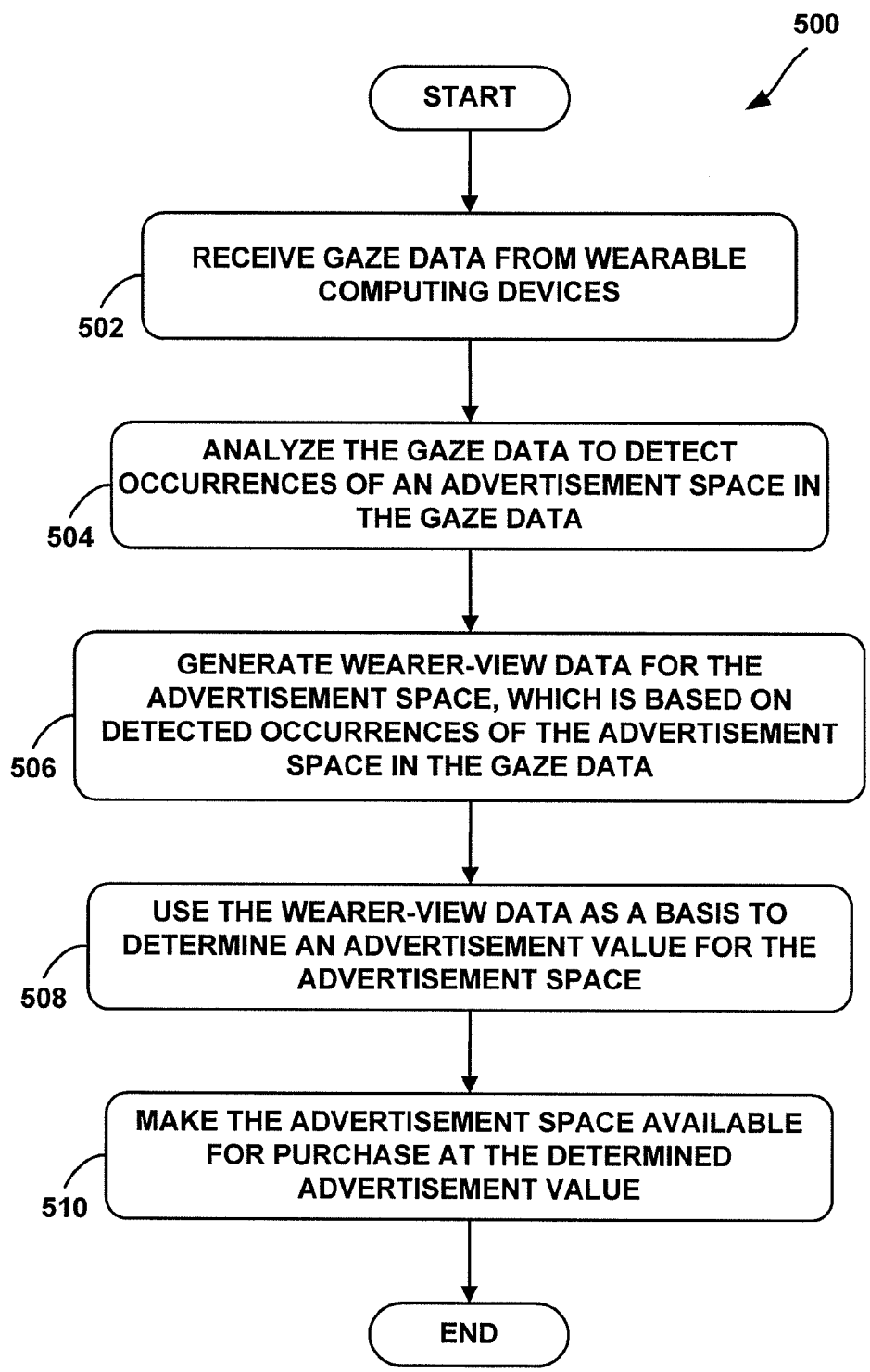
FIG. 5A is a flow chart illustrating a method for determining advertisement value, according to an exemplary embodiment.

FIG. 5A is a flow chart illustrating a method according to an exemplary embodiment. This method may be implemented by a computing device, and in particular, by a server system, in order to value an advertisement space based on point-of-view gaze data received from a number of wearable computing devices (which may be referred to interchangeably as wearable computing devices). Note that wearable computing devices may also be referred to as wearable computers herein. Further, a server system that implements an exemplary method may be referred to as an ad-valuation system, as an ad-valuation server, or simply as a server.

As shown by block 502, method 500 involves a server system receiving gaze data from a number of wearable computing devices. The server system analyzes the gaze data from the wearable computing devices to detect occurrences of an advertisement space in the gaze data, as shown by block 504. The server system then generates wearer-view data for the advertisement space, which is based on detected occurrences of the advertisement space in the gaze data, as shown by block 506. The wearer-view data can then be used as a basis for determining an advertisement value for the advertisement space, as shown by block 508. Once the advertisement value is determined, the server system may cause a computing system to make the advertisement space available for purchase at the determined advertisement value, as shown by block 510.

In an exemplary method 500, the gaze data is received from a number of wearable computing devices. Further, the gaze data from each wearable computing device is generally indicative of a respective wearer-view associated with the given wearable computing device. For example, the gaze data from each wearable computing device may take the form of point-of-view video that is captured at the wearable computing device. As such, the gaze data that is analyzed by the server system may include a number of point-of-view videos (e.g., a respective point-of-view video from each of the wearable computing devices).

The gaze data from some or all of the wearable computing devices that provide gaze data may additionally or alternatively take forms other than point-of-view video. For example, the gaze data from some or all of the wearable computing devices may take the form of respective point-of-view images captured by a forward- or outward-facing camera on the respective wearable computing device. As a specific example, a given wearable computing device may periodically take a picture, and then send the picture to the server system for use in generating wearer view data. To do so, the wearable computing device may analyze point-of-view video for one or more ad spaces, and generate a screen capture of the video when and ad space detected. The wearable computing device may then send the screen capture to the server system. Other examples are also possible.

Since the gaze data from a given wearable computing device is generally indicative of the wearer-view of the wearable computing device's wearer, the gaze data is generally indicative of what the wearer of the device is actually looking at. Further, since the wearer-view data is based on the gaze data, the wearer-view data is indicative of actual views of the ad space by wearers. For instance, the wearer-view data may provide an indication of how many people are looking at a particular advertisement space, which people are actually looking at a particular ad space, when people are looking at a particular ad space, and/or how long people are actually looking at a particular ad space, among other information. As such, the wearer-view data may help to more accurately determine what an advertising space is worth.

As noted above, when occurrences of an ad space are detected in gaze data, an exemplary method 500 may involve generating wearer-view data that is based on the detected occurrences. As such, an exemplary server system 204 may be configured to carry out an exemplary method 500 or portions thereof for many different advertisement spaces. Generally, the accuracy of the ad-space valuation will typically increase as the number of wearable computing devices providing gaze data increases. However, the gaze data may be collected from any number of wearable computing devices without departing from the scope of the invention.

To facilitate determining an advertisement value for a given ad space, the wearer-view data may provide various types of information. For example, the wearer-view data for a given ad space may include, for each detected occurrence of the given ad space: (a) data indicating the particular wearable computing device that provided the gaze data in which the ad space occurred, (b) data indicating a user-profile associated with the particular wearable computing device, (c) data indicating a time of the detected occurrence, (d) a duration of the detected occurrence, and/or (e) other information.

Generally, the function of generating wearer-view data for the advertisement space, as shown in block 506 of method 500, may vary depending upon the information to be included in the wearer-view data. In an exemplary embodiment, detecting an occurrence of an advertising space in the gaze data may serve as a trigger for the server system to generate wearer-view data recording the fact that the occurrence was detected. Further, to generate the wearer-view data for a given occurrence, the server system may extract information from the gaze data in which the occurrence was detected. The extracted information (or information derived from the extracted information) may be included in the wearer-view data generated for the detected occurrence.

A. Per-Occurrence Data for an Ad Space

In some embodiments, the server system 204 may update the wearer-view database 308 upon each detected occurrence of an ad space. For example, the server system may generate a record in the wearer-view database for each detected occurrence of an ad space. In such an embodiment, the record for a given occurrence of an ad space may include: (a) an indication of the particular wearable computing device that provided the gaze data in which the ad space occurred, (b) an indication of a user-profile associated with the particular wearable computing device, (c) a time of the occurrence, and/or (d) a duration of the occurrence.

The wearer-view data for a given occurrence of an ad space may indicate the corresponding wearable computing device that provided the gaze data in which the ad space occurred. In such an embodiment, the server system may determine the corresponding wearable computing device in various ways. For instance, consider an embodiment where the server system receives point-of-view (POV) video stream from a number of wearable computing devices. In such an embodiment, the server system may establish a communication session to receive the video stream from a given one of the wearable computing devices, and as part of establishing and/or participating in the session, may receive an identifier of the wearable computing device. (Note that various protocols, which are well known in the art, may be used to receive a POV video stream and/or to receive other forms of gaze data.) Additionally or alternatively, metadata in the gaze data itself may include an identifier of the wearable computing device that is providing the gaze data.

Other techniques for determining which wearable computing device corresponds to a particular occurrence of an ad space are also possible.

As further noted above, the wearer-view data for a given occurrence of an ad space may indicate an associated user-profile, which is associated with the wearable computing device that provided the gaze data having the particular occurrence. The server system may determine the associated user-profile in various ways. For example, the server may determine the identifier for the corresponding wearable computing device in a manner such as described above or otherwise. The server may then look up a user-profile of a user that is registered to use or is otherwise associated with the corresponding wearable computing device (e.g., by querying a user database that indicates which users are associated with which wearable computing devices). Alternatively, a user-identifier may be provided in the course of receiving the gaze data (e.g., in a communication session or in metadata). In such an embodiment, the server system may use the user-identifier to access a user-profile for the user. As another alternative, the user-profile itself may be received directly from the device (e.g., during the communication session in which the gaze data is received, as metadata included in the gaze data, or in a separate message that is associated with the gaze data). Other techniques for determining a corresponding user-profile for a particular occurrence of an ad space are also possible.

In a further aspect, when the wearer-view data for a given occurrence indicates the associated user-profile, the wearer-view data may simply include an identifier of the associated user-profile. In such an embodiment, the data from such user-profiles may be stored in one or more separate user-profile databases. In this case, the server may use the identifiers of the associated user-profiles to retrieve the data from the actual user-profiles. Alternatively, some or all of the data from the associated user-profile may be included in the wearer-view data for the ad space (e.g., in wearer-view database 308).

In a further aspect, the server system may include a time stamp in the wearer-view data that is generated for a given occurrence. The timestamp may indicate the time at which the occurrence of the ad space was detected. Additionally or alternatively, the timestamp may indicate a time that is derived from time data included in the gaze data. For example, point-of-view video from a given wearable computing device may include time data indicating when the video was recorded by the wearable computing device. As such, the server system may use this time data to generate a timestamp for an occurrence that is detected in such point-of-view video. For instance, the server system may determine a frame or frames of the video that include the ad space, and use a time stamp or time stamps of the frame or frames to generate the timestamp for the detected occurrence. Other techniques for generating a timestamp for a particular occurrence of an ad space are also possible.

In another aspect, the wearer-view data for a given occurrence of an ad space may indicate the duration of the given occurrence. Accordingly, the server system may be configured to determine the duration of a given occurrence of an ad space. For instance, in the above example where POV video includes time data, the server system may use timestamps on frames of the video to determine the duration of time the first frame of the video that includes the ad space and the last subsequent and consecutive frame that includes the ad space. Alternatively, the server system may implement its own timer to determine the duration of a given occurrence of an ad space. Other techniques for determining the duration of a particular occurrence of an ad space are also possible.

In a further aspect, when generating wearer-view data for a given occurrence, the server may consider whether the wearable computing device that corresponds to a given occurrence was being worn during the occurrence. In particular, if the corresponding wearable computing device is not being worn at the time of the detected occurrence, the server may adjust or change the wearer-view data that is generated in response to detecting the occurrence. For example, when the wearable computing device is not being worn, the server may interpret this to mean that the gaze data from the wearable computing device is unlikely to represent what the wearer is actually viewing. Accordingly, the server may include an indication that the wearable computing device was not being worn in the wearer-view data that is created for such an occurrence. Further, server may adjust the wearer-view data so as to decrease the weight of such an occurrence when determining the ad value for the ad space, or may ignore the occurrence entirely (e.g., by refraining from generating any wearer-view data for the occurrence).

B. Summary Data for an Ad Space

In some embodiments, the wearer-view data for a given ad space may include summary data for the ad space such as: (a) a list of which wearable computing devices viewed the ad space (e.g., which wearable computing devices provided gaze data in which one or more occurrences were detected), (b) a list of the user-accounts or the user-profiles that are associated with the wearable computing devices that have viewed the ad space, (c) a total view count indicating the total number of detected occurrences of the ad space, (d) a total view duration of the ad space, (e) an average view duration for occurrences of the ad space, and/or (f) a view rate that indicates how frequently the advertisement space occurs in the gaze data (e.g., occurrences/hour, occurrences/month, etc.). The wearer-view data for a given ad space may additionally or alternatively include other types of summary data for the ad space.

In order to keep the above and other such summary data substantially current, the server system may update the wearer-view data for an ad space each time the ad space is detected in gaze data. For example, when the server system detects an ad space in gaze data from a given wearable computing device, the server system may update the wearer-view data by: (a) adding the given wearable computing device to a list of wearable computing devices that have viewed the ad space (if the wearable computing device is not on the list already), (b) adding the user-account or the user-profile that is associated with the given wearable computing device to a list of user-accounts or user-profiles that have viewed the ad space, (c) incrementing the total view count for the ad space, (d) determining the duration of the occurrence and adding the determined duration to a total view duration for the ad space, and/or (e) determining the duration of the occurrence and adding the determined duration and recalculating the average view duration to account for the determined duration. Other examples are possible as well.

In some embodiments, the wearer-view data for each ad space may include only summary data such as that described above, and thus may not include per-occurrence data for each detected occurrence of an ad space. However, it is also possible that the wearer-view data for a given ad space may include only per-occurrence data, or may include both per-occurrence data and summary data for the ad space.

C. Focus Data for an Occurrence

In some embodiments, the wearer-view data for a given ad space may include focus data, which is generally indicative of the amount of attention paid to an ad space by viewers of the ad space. The focus data may help to provide a more accurate valuation for the ad space by helping take into account the fact that not all views are necessarily equal, since the amount of attention paid to the ad space may vary between views. In such an embodiment, the server system may determine a focus value for a detected occurrence (as described above) when it generates wearer-view data for the occurrence, or may determine a focus value at a later time.

D. Use of Summary Data for Advertisement Valuation

As noted above, an exemplary method 500 may involve using the wearer-view data for an ad space to determine an advertisement value for the advertisement space. Various types of wearer-view data may be utilized when determining an advertisement value. For instance, various types of the summary data described above and/or various types of the per-occurrence data described above may be used to determine the advertisement value for a given ad space. An exemplary valuation method may also incorporate other types of data in addition to wearer-view data. Further, the manner in which a given type of wearer-view data is used to determine an advertisement value may vary depending upon the implementation.

In some embodiments, the ad value for a given ad space may be based on summary data for the ad space. For example, the ad value may be based at least in part on the total view count for an ad space (e.g., the total number of occurrences that are detected in the gaze data). In such an embodiment, the total number of occurrences may be tracked over all time. Alternatively, the total number of occurrences may be tracked over a predetermined period of time (e.g., a year, a month, a week, or a custom-defined time period). In an exemplary embodiment that incorporates total view count, the determined advertisement value will typically increase as the total number of occurrences increases. Further, the manner in which the total view count is used to determine ad value may vary, depending upon the implementation.

As another example, the ad value for a given ad space may be based at least in part on a view rate for the advertisement space (e.g., the rate at which occurrences of the ad space are detected in the gaze data). For instance, the wearer-view data may indicate a number of views per month, per week, per day, per hour, etc. In such an embodiment, the rate may be based on detected occurrences over all time. Alternatively, the rate may be based on occurrences during a predetermined period of time (e.g., during a year, a month, a week, or a custom-defined time period). In an exemplary embodiment that incorporates view rate, the determined advertisement value will typically increase as the view rate increases. Further, the manner in which the view rate is used to determine ad value may vary, depending upon the implementation.

In the above examples, the ad value is determined based on summary data that generally does not differentiate one detected occurrence from another. However, some embodiments may apply further intelligence to account for the fact that some views of an ad space may be more valuable to an advertiser than others.

For example, the ad value for a given ad space may be based at least in part on a total view duration and/or an average view duration for the ad space. In such an embodiment, the total view duration and/or the average view duration may be calculated from all detected occurrences of the ad space or from a representative sample of occurrences. In either case, the total view duration and/or the average view duration may be calculated over all time, or may be calculated over a predetermined period of time (e.g., a year, a month, a week, or a custom-defined time period). In an exemplary embodiment that incorporates total view duration and/or the average view duration, the determined advertisement value will typically increase as the total view duration and/or the average view duration increases. Accordingly, views that last longer will generally contribute more to the ad value and/or be weighted more heavily when determining the ad value. It should be understood that the manner in which the total view duration and/or the average view duration is used to determine ad value may vary, depending upon the implementation.

As another example, the server may determine focus values for all or a representative sample of the detected occurrences of an ad space. The server may then average the focus values for the detected occurrences to determine an average focus value for the ad space. The server can then use the average focus value to determine the ad value for the ad space.

In a further aspect, an exemplary embodiment may help account for the fact that views of an ad space by certain people may be considered more valuable than views of the same ad space by other people. More specifically, in an exemplary embodiment, wearers may opt-in to a program or otherwise give permission for information from their user-profile to be used to value ad spaces. Various types of information from an associated user-profile may then be used to determine how valuable a given occurrence of an ad space is. For instance, a user-profile for a wearer may include: (a) consumer information such as spending habits, locations of purchases, amounts of purchases, types or categories of purchases, timing of purchases, etc., (b) demographic information such as age or age group, ethnicity, nationality, sex, location of residence, and/or location of workplace, (c) contact and/or social networking information such as a wearer's contacts, and possibly data indicating a purchasing influence of the wearer with regard to their contacts (e.g., data indicating any correlation of the wearer's purchasing history to the wearers' friends' purchasing histories), and/or (d) other information such as income, job or job type, other job details, hobbies, interests, and so on.

Therefore, since the occurrence of an ad space in gaze data from a given wearable computing device may be interpreted to mean that the wearer of the given wearable computing device has viewed or is viewing the ad space, information from user-profiles that wearer-view data associates with a given ad space may provide information about the type or types of people that an ad space reaches and/or of the characteristics of people that the ad space reaches. As a result, this information may be used to more accurately determine what types of people are viewing the ad space, and value the ad space accordingly. In particular, an exemplary server may place greater weight on occurrence of an ad space associated with certain people and/or certain types of people when determining the ad value for a given ad space.

For example, the server may determine a respective income level for the user-profile associated with each occurrence. The server may then average the determined income levels to calculate an average income level for viewers of the ad space, and use the average income level as input data to determine the ad value for the ad space. Alternatively, the server may determine an income range of the determined income levels, and use the income range as an input to the ad-value calculation for the ad space. Other examples are also possible.

It should be understood that the ad value for a given ad space may be based upon one type of summary data or a combination of various types of summary data. For example, in one implementation, the total number of views, the view rate, the average view duration, and one or more characteristics of the associated user-profiles, could all be used as inputs when calculating ad value. Many other examples are also possible.

E. Use of Per-Occurrence Ad-Value Contributions for Advertisement Valuation

In some embodiments, a server system may determine an advertisement value for an ad space by first determining an individual advertisement-value contribution for each detected occurrence of the advertisement space. The advertisement-value contribution for a given occurrence may be based on information from the user-profile associated with the occurrence and/or on other information related to the occurrence. The collective knowledge provided by all the individual advertisement-value contributions may then be used to determine the advertisement value for the advertisement space and/or be used to determine summary data for the ad space, which may in turn be used to determine the ad value.

Figure 5B:
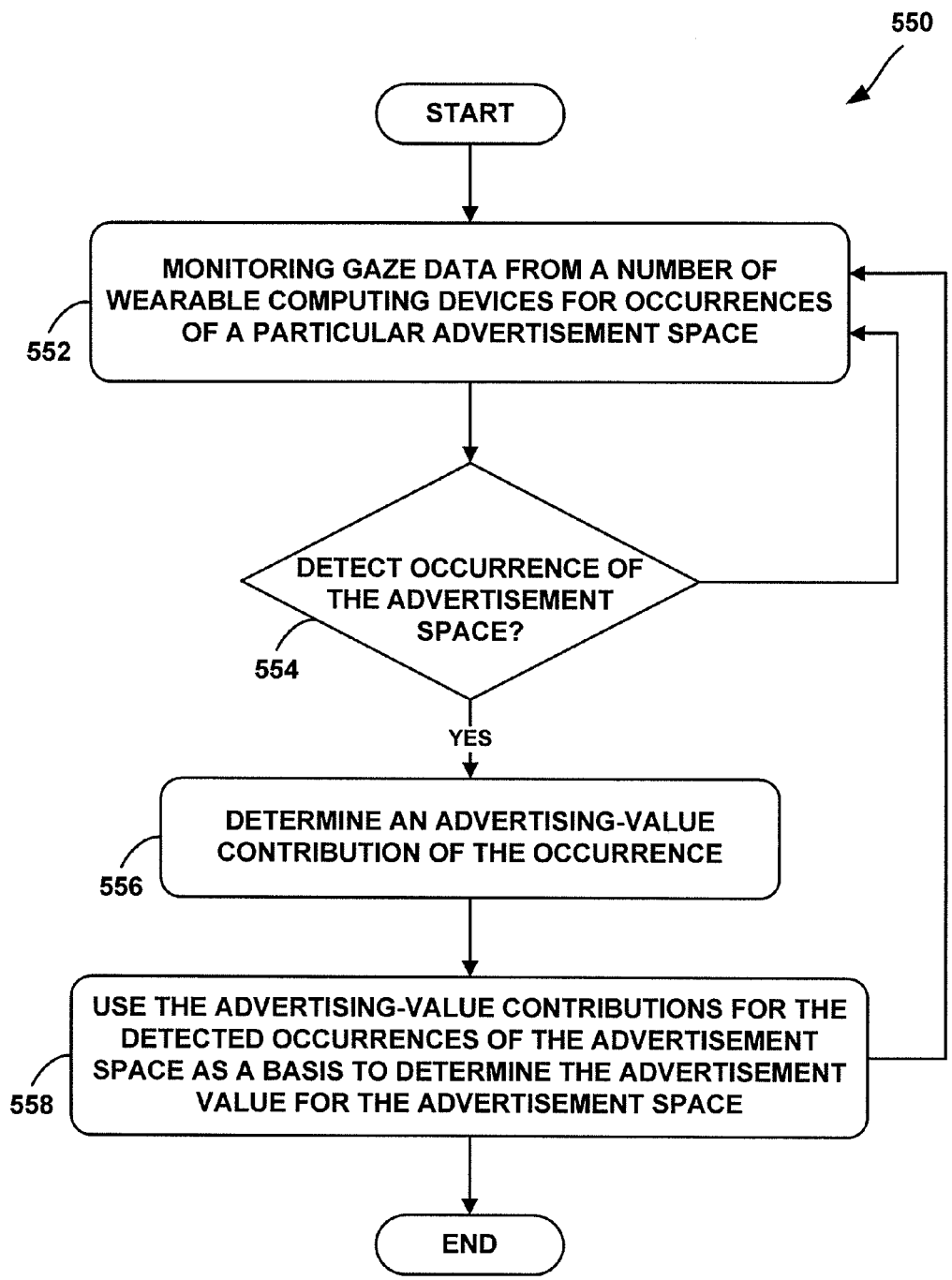
FIG. 5B is a flow chart illustrating a method for determining ad value, according to an exemplary embodiment.

FIG. 5B is a flow chart illustrating a method for determining advertisement value, according to an exemplary embodiment. In particular, FIG. 5B illustrates a method 550 in which the advertisement value for an ad space is based on individual ad-value contributions of occurrences of the ad space in gaze data.

More specifically, method 550 involves monitoring gaze data from a number of wearable computing devices for occurrences of a particular advertisement space, as shown by block 552. Each time an occurrence of the advertisement space is detected, as shown by block 554, the server system may further determine an advertising-value contribution of the occurrence, as shown by block 556. The server system may then determine advertising-value contributions for a number of occurrences by repeating blocks 554 and 556 for a number of detected occurrences of the advertisement space. The server system may then use the advertising-value contributions for the detected occurrences of the advertisement space as a basis for determining the advertisement value for the advertisement space, as shown by block 558.

In some embodiments, such as method 550 of FIG. 5B, the ad-value contribution for each occurrence of an ad space may be determined upon detecting the occurrence in the gaze data. However, it should be understood that the ad-value contribution for some or all occurrences of an ad space may be calculated at a later time, based on wearer-view data that is stored as the occurrences are detected in the gaze data.

A server may use various techniques to determine the individual ad-value contribution for a given occurrence of an ad space in gaze data. Such techniques may utilize various different factors to determine the ad-value contribution for a given occurrence. In some embodiments, the server may use a weighting value for an occurrence to determine the ad-value contribution of the occurrence. In particular, the server may determine a weighting value that generally indicates the particular occurrence's value relative to a "standard" occurrence of the ad space. The weighting value for the particular occurrence may then be applied to a base advertising-value contribution to determine the advertising-value contribution for the particular occurrence. In such an embodiment, the weighting value may be based on various factors or combinations of factors, such as the particular wearable computing device from which the gaze data including the particular occurrence was received, the duration of the occurrence, characteristics of the person who viewed (e.g., as indicated by the user-profile associated with the occurrence), the focus value of the occurrence, and/or other factors.

As a specific example, the ad-value contribution for each occurrence of the ad space may be a dollar amount that is attributed to the occurrence. As such, the server may determine a dollar amount for the ad value by summing the ad-value contributions. As another example, the ad-value contribution for each occurrence of the ad space may be a price rate (e.g., dollars per month, dollars per view, etc.) that is attributed to a respective occurrence of the ad space. As such, the server may determine the ad value by summing the ad-value contributions to get an overall price rate. Other examples are also possible.

Once a server system has determined the individual ad-value contributions for a number of occurrences of the particular ad space, the server may use various techniques to determine the ad value for the ad space. For example, in some embodiments, the server may determine an average advertising-value contribution by averaging the advertising-value contributions of some or all of the detected occurrences. The server may then use the average advertising-value contribution as a basis for determining the advertisement value for the ad space. As a specific example, the server may determine an ad-value contribution for each occurrence in the same manner as the overall price or rate for the ad space, but using the assumption that all occurrences of the ad space are identical to the occurrence. The server may then determine a dollar amount or price rate for the ad space by averaging the ad-value contributions determined in this manner. Other examples are also possible.

It should be understood that techniques described herein for determining an ad value based on the ad-value contributions are not intended to be limiting. Other techniques for determining an ad value based on the ad-value contributions of individual occurrences are also possible, without departing from the scope of the invention.

F. Valuation of an Ad Space on a Per-Advertisement Basis

Some embodiments may involve determining a value an ad space that is specific to a particular type of advertisement. For example, an ad server may determine a value for an ad space when the ad space is used to display an ad for a particular type of product (e.g., for clothing or for a movie).

Further, in some embodiments, an exemplary method may be implemented for ad-specific valuation of an ad space based on the extent to which the ad space reaches the target market of the advertisement. For instance, wearer-view data may be used to determine who is viewing an ad space. The ad space valuation may then be based on the correlation between those who view the ad space and the target market of the specific advertisement.

In such an embodiment, an exemplary method may utilize wearer-view data indicating user-profiles associated with occurrences of an ad space in the gaze data. As such, the server may analyze the associated user-profiles to determine one or more characteristics of those who have viewed the ad space. More specifically, an exemplary method may involve determining a group of user-profiles associated with the advertisement space (e.g., user-profiles that are associated with wearable computing devices that captured the ad space in their respective gaze data). Then, based on characteristics of the associated user-profiles, the server may determine one or more viewer characteristics of the group. The viewer characteristics of the group may be interpreted as indicative of a "standard" viewer of the ad space. As such, the viewer characteristics of the group may incorporate when determining the advertisement value for a specific type advertisement.

For example, some embodiments may involve determining both: (a) the viewer characteristics of the group of associated user-profiles and (b) one or more target-viewer characteristics for the particular advertisement. The server may then compare the viewer characteristics of the group to the target-viewer characteristics and, based on the comparison, determine the advertisement value for the particular advertisement in the advertisement space.

In some embodiments, the ad value for the particular advertisement may be further based on the location of the ad space. In particular, there may be a relationship between the characteristics of a particular advertisement and the location of ad space, and an exemplary method may help to account for such a relationship. In such cases, a weighting factor may be applied to increase or decrease the ad value depending upon the relationship between the location of the ad space and the characteristics of the advertisement.

For example, consider an advertisement for a clothing product and an ad space that is located near to a shopping area and/or near to a store where the clothing product can be purchased. This ad space may generally be considered more valuable when used to display the advertisement for the clothing product than when used to display an ad for a type of product that cannot be purchased nearby. Accordingly, a weighting factor may be applied to increase the ad value for the clothing product in the ad space. Similarly, the weighting factor may function to decrease the ad value for a product that cannot be purchased nearby.

As another example, consider an advertisement for a movie and an ad space that is located near to a movie theater that is showing the movie. This ad space may generally be considered more valuable when used to display the advertisement for the movie than when used to display an ad for a movie that is not in any nearby theaters. Accordingly, a weighting factor may be applied to increase the ad value of the ad space for a movie that is showing in the nearby theater. Similarly, the weighting factor may decrease the ad value for the movie that is not in any nearby theaters. Other examples are also possible.

In a further aspect, some implementations of method 500 may utilize the type of advertisement as the characteristic of the advertisement upon which the ad value is based. In such an embodiment, all advertisements of the same type may be evaluated in the same way. As such, the ad value in such an embodiment may in effect be determined for the type of advertisement in the ad space (rather than specifically for an individual advertisement). Alternatively, the type of advertisement may be one of a number of factors, such that an ad space may be valued differently for different advertisements that are classified as being the same type of advertisement.

G. Adjusting the Ad Value Based on other Factors

In some embodiments, ad valuation may be based on other types of data, in addition to wearer-view data. In such an embodiment, the ad server may determine a base value for the advertisement, or a weighting to be applied to the ad value based on an intrinsic value of the ad space, which accounts for the characteristics of the ad space itself, and then adjust the intrinsic value according to the wearer-view data.

For example, in some embodiments, an exemplary method may use the geographic location of the advertisement space as a further basis for determining the advertisement value for the advertisement space. For example, an advertisement that is located in a shopping area may have a greater intrinsic value than one that is located in an alley. Accordingly, an ad value that is determined based on wearer-view data may be adjusted based on the location of the ad space. Other examples are also possible. Generally, the type and/or the amount of adjustment that is applied due to the location of an ad space may vary depending upon the particular implementation.

Further, in some embodiments, the server may consider the type of advertisement space and/or the format in which advertisements can be displayed in the ad space when determining the advertisement value for the advertisement space. For example, an LCD billboard might generally be considered more valuable than an equivalent print billboard. As such, when an ad value is determined for a billboard based on wearer-view data, the determined ad value may be adjusted based on whether the billboard is an LCD or a print billboard. Other examples are also possible. Generally, the type and/or the amount of adjustment that is applied based on the type of advertisement space may vary depending upon the particular implementation. Further, other adjustments, based on other characteristics of an ad space, are also possible.

In another aspect, an ad space may be blank (e.g., not displaying an advertisement) during some or all of the period in which gaze data is being collected for purposes of determining the ad value. The fact that an ad space is blank, as opposed to displaying an advertisement, may affect the gaze data for the ad space because a blank space might attract less attention from nearby people. Further, different advertisements may attract different amounts of attention. Therefore, when an advertisement is displayed while gaze data is being collected, the particular advertisement may itself affect the gaze data. As such, it is possible that wearer-view data for an ad space may be effected by whether or not an ad space is blank, and if something is displayed in the ad space, what specifically is displayed.

Accordingly, an exemplary method may further involve determining a pre-sale weighting factor for an advertisement space, which is based on: (a) whether the ad space is blank while gaze data is being collected and/or (b) the characteristics of what is displayed in the ad space while gaze data is being collected. A server may then use the pre-sale weighting factor for the ad space as a further basis for determining the advertisement value for the advertisement space.

As a specific example, an exemplary method may further the server determining whether or not the advertisement space had an advertisement in place while receiving and analyzing the gaze data. Then, if the advertisement space had an advertisement in place, the server may apply a first adjustment to the wearer-view data before using the wearer-view data to determine the advertisement value (e.g., an adjustment or weighting factor that corresponds to the particular advertisement that is displayed). On the other hand, if an advertisement was not displayed in the advertisement space, then the server may apply a second adjustment to the wearer-view data (e.g., an adjustment that accounts for the fact that no advertisement was displayed).

In such an embodiment, the server may determine whether or not the advertisement space had an advertisement in place in various ways. For example, the server may query an ad space database to determine whether the ad space is in use and if so, what advertisement is being displayed. Additionally or alternatively, the server may analyze the gaze data itself (e.g., by analyzing point-of-view video in which the ad space is detected). Other examples are also possible.

In yet another aspect, some embodiments may implement gaze-data requirements that require a certain amount of gaze data be analyzed before an ad space can be offered for sale in an ad-marketplace system. For instance, an ad-marketplace system may require that gaze data from a threshold number of devices have been analyzed before the determined ad value is deemed accurate enough to offer the ad space for sale via the marketplace. Additionally or alternatively, ad-marketplace system may require that gaze data be monitored for a certain period of time (e.g., at least a week) before the determined ad value is deemed accurate enough to offer the ad space for sale.

Further, in some embodiments, wearer-view data requirements may require that a certain amount of wearer-view data be generated before an ad space can be offered for sale in an ad-marketplace system. For example, an ad-marketplace system may require that a certain number of occurrences of an ad space be detected before the determined ad value is deemed accurate enough to offer the ad space for sale via the marketplace (or in other words, require that the wearer-view data takes into account at least a threshold number of occurrences). Other examples are also possible.

VIII. Use of Supplemental Gaze Data from Non-Wearable Computing Devices

In some embodiments, an exemplary method may incorporate supplemental gaze data from one or more non-wearable computing devices. In such an embodiment, the supplemental gaze data may include media captured by the non-wearable computing devices. For example, supplemental gaze data may be received from mobile phones, tablet computers, network-enabled video and/or still cameras, and/or other non-wearable computing devices.

Similar to the gaze data from wearable computing devices, the supplemental gaze data is generally indicative of a respective user-view associated with a device that provides supplemental gaze data. Accordingly, an exemplary method may further involve receiving supplemental gaze data from one or more non-wearable computing devices that are registered to a given user-account. A server may then detect additional occurrences of advertisement spaces in the supplemental gaze data, and factor the additional occurrences in when determining the gaze value for the user-account.

However, because supplemental gaze data is captured at non-wearable devices, supplemental gaze data may less reliably represent what the user actually sees, as compared to gaze data captured by a wearable device that is physically worn on the user's person. Accordingly, in an exemplary method, the server may weight supplemental occurrences that are detected in the supplemental gaze data in order to account for the increased probability that the supplemental gaze data does not represent what the user actually sees. For example, the server may weight a supplemental occurrence by a significance factor corresponding to the likelihood that the corresponding supplemental gaze data is indicative of a respective user-view associated with the non-wearable computing device that provided the supplemental gaze data in which the supplemental occurrence was detected.

In a further aspect, systems may be implemented to actively search supplemental gaze data that is pre-recorded, such as image libraries that are accessible via a network. For example, a server or an associated system may be configured to analyze images from one or more online image albums to determine supplemental user-view data for the advertisement space. In such an embodiment, the supplemental user-view data is based on occurrences of the advertisement space in the plurality of images.

For example, the system may search image albums on a photo-sharing website, social-network website, or another network source, for occurrences of the ad space in the images. When an occurrence is found, the system may generate supplemental user-view data for the occurrence. For instance, many such websites require that users open a user-account in order to create photo albums and/or share photos. Accordingly, the system may store data linking the occurrence of the ad space to the user-account via which the image was shared.

In a further aspect, one image of an ad space may be indicative of a more valuable view of the ad space than another image. As such, each image that includes the ad space may be evaluated for indications of how significant the occurrence is, so that the occurrence may be weighted accordingly when determining the ad value.

For example, an exemplary method may involve analyzing one or more images from one or more image albums to detect any occurrences of the advertisement space in the images. Then, for each image where an advertisement space is detected, the system may determine a gaze-value contribution and/or an advertising-value contribution for the given image (note that in some instances, the advertising-value contribution may be used as the gaze-value contribution). As a specific example, determining a prominence value corresponding to a prominence of the advertisement space in the given image (e.g., a size and/or location of the ad space in the image), and then use the prominence value as a basis for determining a gaze-value contribution and/or an advertising-value contribution for the given image. The system may then use any gaze-value contributions from these images, such as any prominence values that are determined for any of the images, when determining the gaze value for the associated user-account. Similarly, the system may use any advertising-value contributions from these images, such as any prominence values that are determined for any of the images, when determining the advertisement value for the advertisement space.

In a further aspect, data from GPS systems and other sensors, such as magnetometers, accelerometers, and/or gyroscopes may provide supplemental gaze data. In some embodiments, GPS on a wearable computing device or another device (e.g., a mobile phone or tablet) may provide an indication of location, and a magnetometer on the same device may provide an indication of orientation, such that it may be inferred that a user of the device is in a certain location and is facing a certain direction. Further, the location of an ad space may also be determined as described herein. Thus, if the user is inferred to be facing a location where and space is located, this may be considered a view of the ad space, and thus may be factored into the wearer-view data. Other examples of using GPS and/or sensor data to infer supplemental gaze data are also possible.

IX. Wearable-Computer-Based Functionality

The above-described methods and systems are generally described with reference to examples where wearable computing devices collect and send gaze data to an ad-valuation server system, such that the server system provides most of the functionality as far as detecting ad spaces in gaze data, determining individual gaze values, and/or determining ad values for ad spaces. This arrangement may be referred to as a "cloud-based" embodiment. However, it should be understood that wearable-computer-based embodiments and partially cloud-based embodiments are also possible. Thus, it should be understood that some or all of the functionality that is described herein as being carried out by a server may alternatively be carried out at one or more wearable computing devices.

Figure 6:
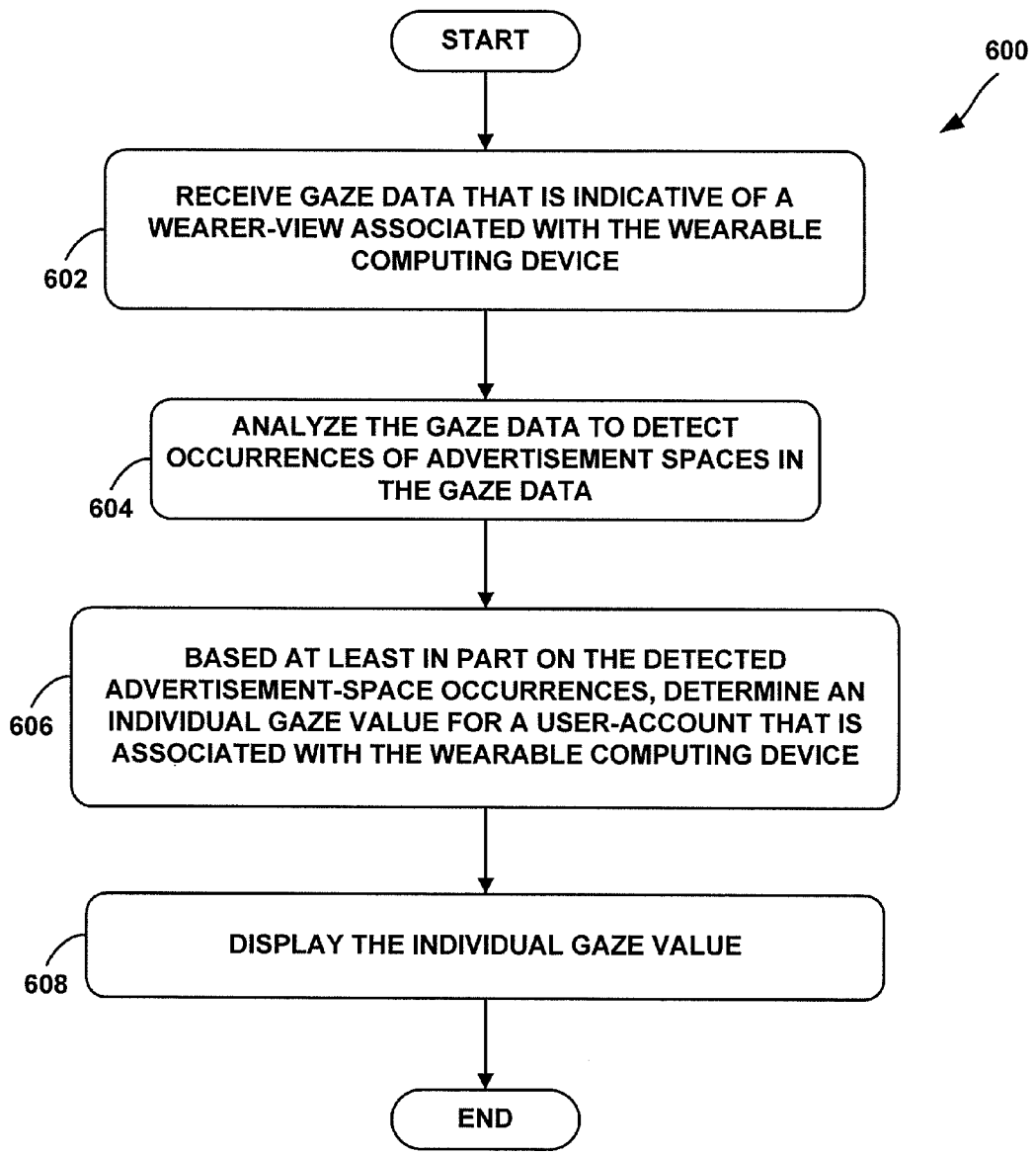
FIG. 6 is a flow chart illustrating a method that may be carried out at a wearable computing device, according to an exemplary embodiment.

For example, FIG. 6 is a flow chart illustrating a method that may be carried out at a wearable computing device, according to an exemplary embodiment. As shown by block 602, method 600 involves a wearable computing device receiving gaze data that is indicative of a wearer-view associated with the wearable computing device. At block 604, the wearable computing device analyzes the gaze data to detect occurrences of advertisement spaces in the gaze data. Based at least in part on the detected advertisement-space occurrences, the wearable computing device may determine an individual gaze value for a user-account that is associated with the wearable computing device, as shown by block 606.

The wearable computing device may then send the individual gaze value for display, as shown by block 608. For example, the wearable computing device may simply send the gaze value for display in its own display (e.g., in an HMD), or may send the gaze value to another computing device of the wearer (e.g., a mobile phone, tablet, or laptop computer). Other examples are also possible.

The function of analyzing gaze data for occurrences of advertisement spaces may be accomplished in various ways. In some embodiments, the wearable computing device may monitor gaze data as it is generated, so that occurrences of ad spaces can be detected in real-time. In other embodiments, the wearable computing device may store gaze data and then later search for occurrences of advertisement spaces in the gaze data. In yet other embodiments, a wearable computing device may implement a combination of real-time analysis and after-the-fact analysis of stored gaze data. For instance, the wearable computing device may search for some ad spaces in real-time, as well as storing some or all gaze data so that, if needed, the wearable computing device can search for other ad spaces at a later time. Other techniques are also possible.

In a further aspect, the processing and/or storage capabilities of individual wearable computing devices may be limited as compared to a server system. As such, when a wearable computing device stores gaze data for analysis at a later time, the wearable computing device may take various actions to reduce the size of the gaze data before storing the gaze data. For instance, rather than store full-size point-of-view video that is captured at the wearable computing device, the wearable computing device may periodically generate and store screenshots from the point-of-view video. Alternatively, the wearable computing device may apply compression, and/or may reduce the resolution and/or frame-rate of the POV video, before storing the video. As another alternative, the wearable computing device may implement real-time analysis of the gaze data for occurrences of ad spaces, and also send the gaze data to the server to be stored in the event further analysis is needed at a later time.

In a variation on method 600, the wearable computing device may notify the server each time it detects an occurrence of ad space in its gaze data, so that the server can use the detected occurrence when determining a gaze value for the user-account associated with the wearable computing device. In such an embodiment, the server may determine a gaze-value contribution of each occurrence that is indicated by the wearable computing device, and use all or a subset of these gaze-value contributions to determine the individual gaze value for the user-account.

In a further aspect, when a wearable computing device detects an ad space in its gaze data, the wearable computing device may determine whether it is being worn when the ad space is detected. The wearable computing device may then adjust or change the manner in which such an occurrence of an ad space is used to determine the individual gaze value, in the event the wearable computing device is not being worn at the time of the detected occurrence. For example, if the wearable computing device is not being worn when an ad space is detected, this may be interpreted to mean that the gaze data that included the ad space is unlikely to represent what the wearer is actually viewing. Accordingly, the wearable computing device may reduce the significance of the occurrence when determining the individual gaze value for the occurrence, or may ignore the occurrence entirely (e.g., by refraining from generating any wearer-view data based on the occurrence). Alternatively, in an embodiment where the wearable computing device notifies the server system of detected occurrences, the wearable computing device may notify the server system that the wearable computing device was not being worn when the particular occurrence was detected, or may simply refrain from notifying the server of ad-space occurrence while the wearable computing device is not being worn.

Further, in embodiments where the wearable computing device notifies the server of detected ad-space occurrences, the wearable computing device may notify the server when the wearable computing device is not being worn during an occurrence. Alternatively, in such an embodiment, the wearable computing device may simply refrain from notifying the server about the particular occurrence and/or may refrain from sending wearer-view data to the server that is based on the particular occurrence.

Yet further, the wearable computing device may use various techniques to determine whether or not the wearable computing device is being worn. For example, the wearable computing device may use various sensors, such as accelerometers, gyroscopes, and/or compasses, to determine whether the position and/or motions of the wearable computing device are characteristic of the wearable computing device being worn. Additionally or alternatively, the wearable computing device may use various sensors to determine whether the wearable computing device is in contact with a wearer's skin or positioned on the wearer's face. More generally, the wearable computing device may use any technique that is now known or later developed to determine whether the wearable computing device is being worn.

X. Exemplary Wearable Computing Systems

Figure 7A:
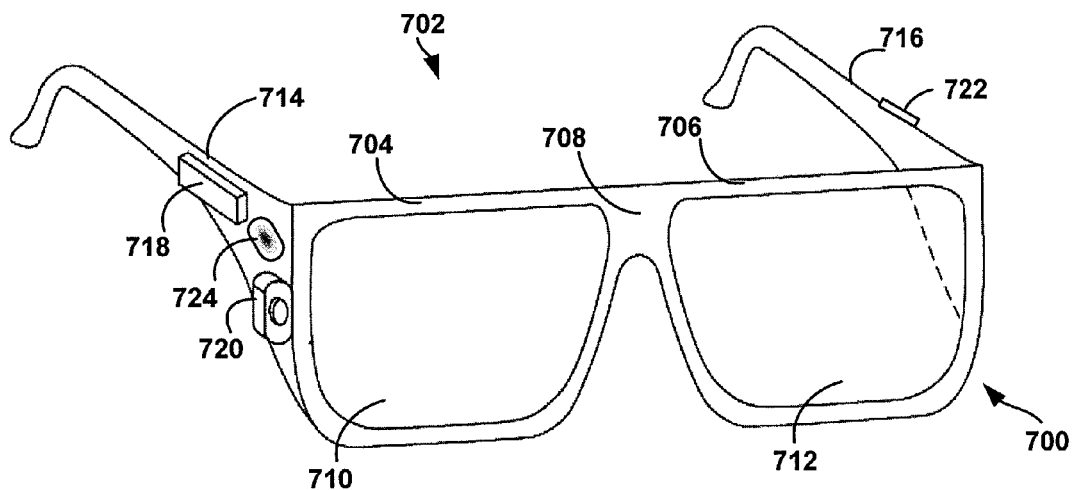
FIG. 7A illustrates a wearable computing system according to an exemplary embodiment.

FIG. 7A illustrates a wearable computing system according to an exemplary embodiment. In FIG. 7A, the wearable computing system takes the form of a head-mounted device (HMD) 702 (which may also be referred to as a head-mounted display or a heads-up display (HUD)). It should be understood, however, that exemplary systems and devices may take the form of or be implemented within or in association with other types of devices, without departing from the scope of the invention. As illustrated in FIG. 7A, the head-mounted device 702 comprises frame elements including lens-frames 704, 706 and a center frame support 708, lens elements 710, 712, and extending side-arms 714, 716. The center frame support 708 and the extending side-arms 714, 716 are configured to secure the head-mounted device 702 to a user's face via a user's nose and ears, respectively.

Each of the frame elements 704, 706, and 708 and the extending side-arms 714, 716 may be formed of a solid structure of plastic and/or metal, or may be formed of a hollow structure of similar material so as to allow wiring and component interconnects to be internally routed through the head-mounted device 702. Other materials may be possible as well.

One or more of each of the lens elements 710, 712 may be formed of any material that can suitably display a projected image or graphic. Each of the lens elements 710, 712 may also be sufficiently transparent to allow a user to see through the lens element. Combining these two features of the lens elements may facilitate an augmented reality or heads-up display where the projected image or graphic is superimposed over a real-world view as perceived by the user through the lens elements.

The extending side-arms 714, 716 may each be projections that extend away from the lens-frames 704, 706, respectively, and may be positioned behind a user's ears to secure the head-mounted device 702 to the user. The extending side-arms 714, 716 may further secure the head-mounted device 702 to the user by extending around a rear portion of the user's head. Additionally or alternatively, for example, the HMD 702 may connect to or be affixed within a head-mounted helmet structure. Other possibilities exist as well.

The HMD 702 may also include an on-board computing system 718, a video camera 720, a sensor 722, and a finger-operable touch pad 724. The on-board computing system 718 is shown to be positioned on the extending side-arm 714 of the head-mounted device 702; however, the on-board computing system 718 may be provided on other parts of the head-mounted device 702 or may be positioned remote from the head-mounted device 702 (e.g., the on-board computing system 718 could be wire- or wirelessly-connected to the head-mounted device 702). The on-board computing system 718 may include a processor and memory, for example. The on-board computing system 718 may be configured to receive and analyze data from the video camera 720 and the finger-operable touch pad 724 (and possibly from other sensory devices, user interfaces, or both) and generate images for output by the lens elements 710 and 712.

The video camera 720 is shown positioned on the extending side-arm 714 of the head-mounted device 702; however, the video camera 720 may be provided on other parts of the head-mounted device 702. The video camera 720 may be configured to capture images at various resolutions or at different frame rates. Many video cameras with a small form-factor, such as those used in cell phones or webcams, for example, may be incorporated into an example of the HMD 702.

Further, although FIG. 7A illustrates one video camera 720, more video cameras may be used, and each may be configured to capture the same view, or to capture different views. For example, the video camera 720 may be forward- or outward-facing to capture at least a portion of the real-world view perceived by the user. This forward facing image captured by the video camera 720 may then be used to generate an augmented reality where computer generated images appear to interact with the real-world view perceived by the user.

The sensor 722 is shown on the extending side-arm 716 of the head-mounted device 702; however, the sensor 722 may be positioned on other parts of the head-mounted device 702. The sensor 722 may include one or more of a gyroscope or an accelerometer, for example. Other sensing devices may be included within, or in addition to, the sensor 722 or other sensing functions may be performed by the sensor 722.

The finger-operable touch pad 724 is shown on the extending side-arm 714 of the head-mounted device 702. However, the finger-operable touch pad 724 may be positioned on other parts of the head-mounted device 702. Also, more than one finger-operable touch pad may be present on the head-mounted device 702. The finger-operable touch pad 724 may be used by a user to input commands. The finger-operable touch pad 724 may sense at least one of a position and a movement of a finger via capacitive sensing, resistance sensing, or a surface acoustic wave process, among other possibilities. The finger-operable touch pad 724 may be capable of sensing finger movement in a direction parallel or planar to the pad surface, in a direction normal to the pad surface, or both, and may also be capable of sensing a level of pressure applied to the pad surface. The finger-operable touch pad 724 may be formed of one or more translucent or transparent insulating layers and one or more translucent or transparent conducting layers. Edges of the finger-operable touch pad 724 may be formed to have a raised, indented, or roughened surface, so as to provide tactile feedback to a user when the user's finger reaches the edge, or other area, of the finger-operable touch pad 724. If more than one finger-operable touch pad is present, each finger-operable touch pad may be operated independently, and may provide a different function.

Figure 7B:
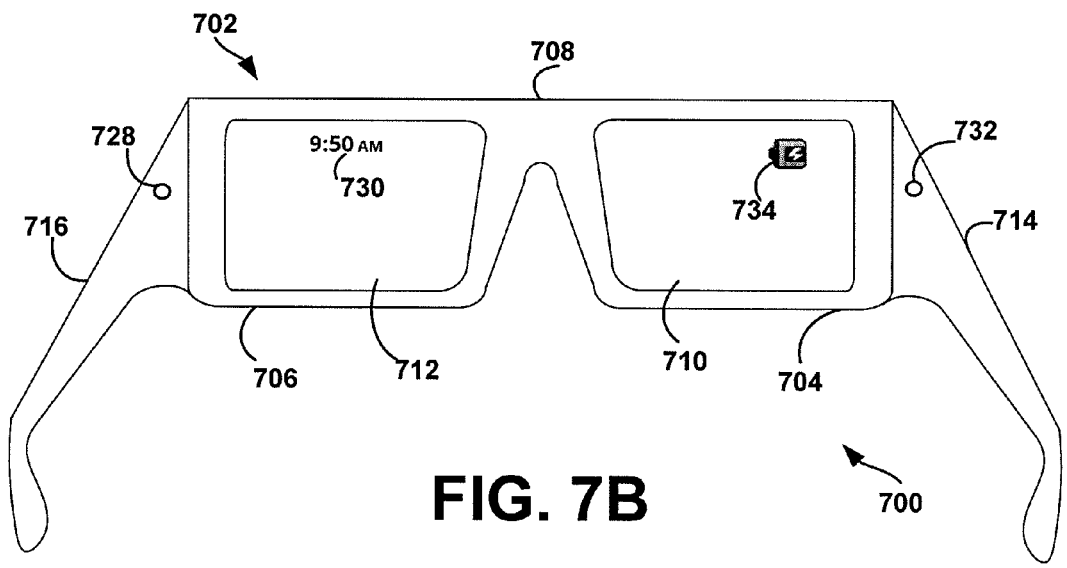
FIG. 7B illustrates an alternate view of the wearable computing device illustrated in FIG. 7A.

FIG. 7B illustrates an alternate view of the wearable computing device illustrated in FIG. 7A. As shown in FIG. 7B, the lens elements 710, 712 may act as display elements. The head-mounted device 702 may include a first projector 728 coupled to an inside surface of the extending side-arm 716 and configured to project a display 730 onto an inside surface of the lens element 712. Additionally or alternatively, a second projector 732 may be coupled to an inside surface of the extending side-arm 714 and configured to project a display 734 onto an inside surface of the lens element 710.

The lens elements 710, 712 may act as a combiner in a light projection system and may include a coating that reflects the light projected onto them from the projectors 728, 732. In some embodiments, a reflective coating may not be used (e.g., when the projectors 728, 732 are scanning laser devices).

In alternative embodiments, other types of display elements may also be used. For example, the lens elements 710, 712 themselves may include: a transparent or semi-transparent matrix display, such as an electroluminescent display or a liquid crystal display, one or more waveguides for delivering an image to the user's eyes, or other optical elements capable of delivering an in focus near-to-eye image to the user. A corresponding display driver may be disposed within the frame elements 704, 706 for driving such a matrix display. Alternatively or additionally, a laser or LED source and scanning system could be used to draw a raster display directly onto the retina of one or more of the user's eyes. Other possibilities exist as well.

Figure 8A:
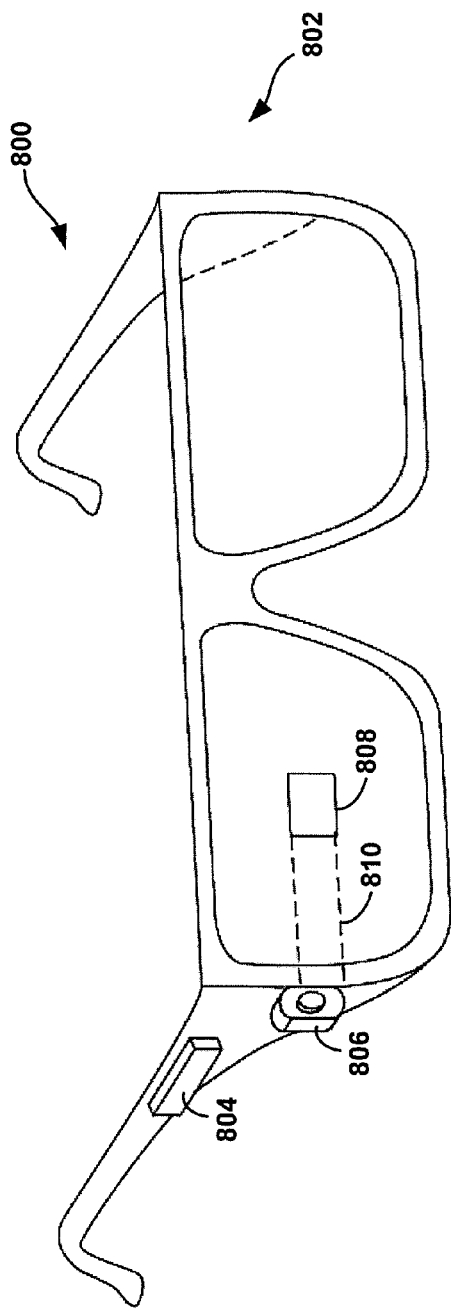
FIG. 8A illustrates another wearable computing system according to an exemplary embodiment.

FIG. 8A illustrates another wearable computing system according to an exemplary embodiment, which takes the form of an HMD 802. The HMD 802 may include frame elements and side-arms such as those described with respect to FIGS. 7A and 7B. The HMD 802 may additionally include an on-board computing system 804 and a video camera 806, such as those described with respect to FIGS. 7A and 7B. The video camera 806 is shown mounted on a frame of the HMD 802. However, the video camera 806 may be mounted at other positions as well.

As shown in FIG. 8A, the HMD 802 may include a single display 808 which may be coupled to the device. The display 808 may be formed on one of the lens elements of the HMD 802, such as a lens element described with respect to FIGS. 7A and 7B, and may be configured to overlay computer-generated graphics in the user's view of the physical world. The display 808 is shown to be provided in a center of a lens of the HMD 802, however, the display 808 may be provided in other positions. The display 808 is controllable via the computing system 804 that is coupled to the display 808 via an optical waveguide 810.

Figure 8B:
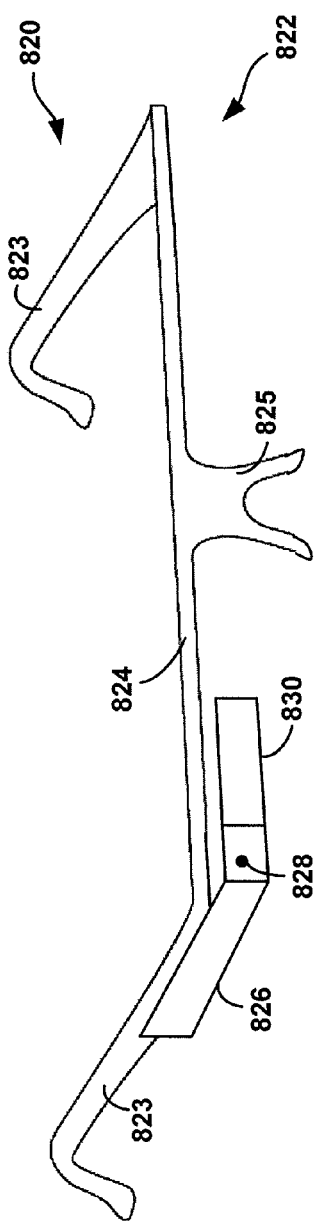
FIG. 8B illustrates another wearable computing system according to an exemplary embodiment.

FIG. 8B illustrates another wearable computing system according to an exemplary embodiment, which takes the form of an HMD 822. The HMD 822 may include side-arms 823, a center frame support 824, and a bridge portion with nosepiece 825. In the example shown in FIG. 8B, the center frame support 824 connects the side-arms 823. The HMD 822 does not include lens-frames containing lens elements. The HMD 822 may additionally include an on-board computing system 826 and a video camera 828, such as those described with respect to FIGS. 7A and 7B.

The HMD 822 may include a single lens element 830 that may be coupled to one of the side-arms 823 or the center frame support 824. The lens element 830 may include a display such as the display described with reference to FIGS. 7A and 7B, and may be configured to overlay computer-generated graphics upon the user's view of the physical world. In one example, the single lens element 830 may be coupled to the inner side (i.e., the side exposed to a portion of a user's head when worn by the user) of the extending side-arm 823. The single lens element 830 may be positioned in front of or proximate to a user's eye when the HMD 822 is worn by a user. For example, the single lens element 830 may be positioned below the center frame support 824, as shown in FIG. 8B.

FIG. 9 illustrates a schematic drawing of a wearable computing device according to an exemplary embodiment. In system 900, a device 910 communicates using a communication link 920 (e.g., a wired or wireless connection) to a remote device 930. The device 910 may be any type of device that can receive data and display information corresponding to or associated with the data. For example, the device 910 may be a heads-up display system, such as the head-mounted devices 102, 802, or 822 described with reference to FIGS. 7A-9.

Thus, the device 910 may include a display system 912 comprising a processor 914 and a display 916. The display 910 may be, for example, an optical see-through display, an optical see-around display, or a video see-through display. The processor 914 may receive data from the remote device 930, and configure the data for display on the display 916. The processor 914 may be any type of processor, such as a micro-processor or a digital signal processor, for example.

The device 910 may further include on-board data storage, such as memory 918 coupled to the processor 914. The memory 918 may store software that can be accessed and executed by the processor 914, for example.

The remote device 930 may be any type of computing device or transmitter including a laptop computer, a mobile telephone, or tablet computing device, etc., that is configured to transmit data to the device 910. The remote device 930 and the device 910 may contain hardware to enable the communication link 920, such as processors, transmitters, receivers, antennas, etc.

In FIG. 9, the communication link 920 is illustrated as a wireless connection; however, wired connections may also be used. For example, the communication link 920 may be a wired serial bus such as a universal serial bus or a parallel bus. A wired connection may be a proprietary connection as well. The communication link 920 may also be a wireless connection using, e.g., Bluetooth® radio technology, communication protocols described in IEEE 802.11 (including any IEEE 802.11 revisions), Cellular technology (such as GSM, CDMA, UMTS, EV-DO, WiMAX, or LTE), or Zigbee® technology, among other possibilities. The remote device 930 may be accessible via the Internet and may include a computing cluster associated with a particular web service (e.g., social-networking, photo sharing, address book, etc.).

It should be understood that for situations in which the embodiments discussed herein collect and/or use any personal information about users or information that might relate to personal information of users, the users may be provided with an opportunity to opt in/out of programs or features that involve such personal information (e.g., information about a user's preferences or a user's contributions to social content providers). In addition, certain data may be anonymized in one or more ways before it is stored or used, so that personally identifiable information is removed. For example, a user's identity may be anonymized so that no personally identifiable information can be determined for the user and so that any identified user preferences or user interactions are generalized (for example, generalized based on user demographics) rather than associated with a particular user.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A computer-implemented method comprising:
receiving, by a computing device, gaze data that is indicative of a wearer-view associated with a first wearable computing device, wherein the wearable computing device is associated with a first user-account;
analyzing, by the computing device, the gaze data to detect one or more occurrences of one or more advertisement spaces in the gaze data, wherein the one or more detected advertisement-space occurrences are indicative of one or more viewings of the one or more advertisement spaces that are associated with the first user-account;
determining, by the computing device, at least one context associated with the wearable computing device;
based at least in part on (a) the one or more detected advertisement-space occurrences, and (b) the at least one context associated with the wearable computing device the computing device, the computing device determining an individual gaze value for the first user-account; and
sending, by the computing device, a gaze-value indication, wherein the gaze-value indication indicates the individual gaze value for the first user-account.

2. The method of claim 1, wherein the individual gaze value indicates a value provided to one or more advertisers from the one or more advertisement-space viewings that are associated with the first account.

3. The method of claim 1, further comprising:
receiving, by the computing device, supplemental gaze data that is indicative of a wearer-view associated with at least one other computing device, wherein the at least one other computing device is also associated with the first user-account;

analyzing the supplemental gaze data to detect one or more occurrences of at least one advertisement space in the gaze data; and using the one or more occurrences of the at least one advertisement space detected in the supplemental gaze data as a further basis for determining the individual gaze value for the first user-account.

4. The method of claim 3, wherein the at least one other computing device comprises one or more of: (a) a mobile phone and (b) a tablet computer.

5. The method of claim 1, wherein the gaze data comprises a point-of-view image data captured at the wearable computing device.

6. The method of claim 1, wherein the wearable computing device comprises a head-mounted display (HMD) that includes an outward-facing camera, and wherein the point-of-view image data is captured by the outward-facing camera.

7. The method of claim 1, wherein determining the individual gaze value for the first user-account comprises:
for each of the one or more detected occurrences of an advertisement in the gaze data, determining a gaze-value contribution of the detected occurrence; and
using the one or more gaze-value contributions for the one or more detected occurrences as a basis for determining the individual gaze value for the user-account.

8. The method of claim 1, wherein determining the individual gaze value for the first user-account comprises:
for one or more of the one or more detected occurrences of an advertisement in the gaze data: (a) determining a context associated with the user-account at or near a time of the detected occurrence, and (b) determining a gaze-value contribution of the detected occurrence based at least in part on the context associated with the user-account at or near the time of the detected occurrence; and
using the one or more gaze-value contributions for the one or more detected occurrences as a basis for determining the individual gaze value for the user-account.

9. The method of claim 8, wherein determining the gaze-value contribution of at least one detected occurrence comprises:
using the gaze data as a basis for determining a focus value corresponding to the at least one detected occurrence of the given advertisement space, wherein the focus value is indicative of attention paid to the given advertisement space during the occurrence; and
using the focus value as a basis for determining the gaze-value contribution of the at least one detected occurrence.

10. The method of claim 9, wherein determining the focus value corresponding to the at least one detected occurrence comprises:
determining movement of the given advertisement space during the at least one detected occurrence; and
using the determined movement of the given advertisement space as a basis for determining the focus value for the at least one detected occurrence.

11. A system comprising:
at least one processor;
a non-transitory computer-readable medium; and
program instructions stored on the non-transitory computer-readable medium and executable by the at least one processor to:

receive gaze data that is indicative of a wearer-view associated with a first wearable computing device, wherein the wearable computing device is associated with a first user-account;
analyze the gaze data to detect one or more occurrences of one or more advertisement spaces in the gaze data, wherein the one or more detected advertisement-space occurrences are indicative of one or more viewings of the one or more advertisement spaces that are associated with the first user-account;
determine at least one context associated with the wearable computing device;
based at least in part on (a) the one or more detected advertisement-space occurrences, and (b) the at least one context associated with the wearable computing device the computing device, determine an individual gaze value for the first user-account; and
send a gaze-value indication, wherein the gaze-value indication indicates the individual gaze value for the first user-account.

12. The system of claim 11, further comprising program instructions stored on the non-transitory computer-readable medium and executable by the at least one processor to:
receive supplemental gaze data that is indicative of a wearer-view associated with at least one other computing device, wherein the at least one other computing device is also associated with the first user-account;
analyze the supplemental gaze data to detect one or more occurrences of at least one advertisement space in the gaze data; and
use the one or more occurrences of the at least one advertisement space detected in the supplemental gaze data as a further basis to determine the individual gaze value for the first user-account.

13. The system of claim 12, wherein the at least one other computing device comprises one or more of: (a) a mobile phone and (b) a tablet computer.

14. The system of claim 11, wherein the gaze data comprises a point-of-view image data captured at the wearable computing device.

15. The system of claim 14, wherein the wearable computing device comprises a head-mounted display (HMD) that includes an outward-facing camera, and wherein the point-of-view image data is captured by the outward-facing camera.

16. The system of claim 11, wherein the program instructions stored on the non-transitory computer-readable medium and executable by the at least one processor to determine the individual gaze value for the first user-account comprise program instructions stored on the non-transitory computer-readable medium and executable by the at least one processor to:
for each of the one or more detected occurrences of an advertisement in the gaze data, determine a gaze-value contribution of the detected occurrence; and
use the one or more gaze-value contributions for the one or more detected occurrences as a basis to determine the individual gaze value for the user-account.

17. The system of claim 11, wherein the program instructions stored on the non-transitory computer-readable medium and executable by the at least one processor to determine the individual gaze value for the first user-account comprise program instructions stored on the non-transitory computer-readable medium and executable by the at least one processor to:
for one or more of the one or more detected occurrences of an advertisement in the gaze data: (a) determine a context associated with the user-account at or near a time of the detected occurrence, and (b) determine a gaze-value contribution of the detected occurrence based at least in part on the context associated with the user-account at or near the time of the detected occurrence; and use the one or more gaze-value contributions for the one or more detected occurrences as a basis to determine the individual gaze value for the user-account.

18. The system of claim 17, wherein program instructions stored on the non-transitory computer-readable medium and executable by the at least one processor to determine the gaze-value contribution of at least one detected occurrence comprise program instructions stored on the non-transitory computer-readable medium and executable by the at least one processor to:

use the gaze data as a basis to determine a focus value corresponding to the at least one detected occurrence of the given advertisement space, wherein the focus value is indicative of attention paid to the given advertisement space during the occurrence; and use the focus value as a basis to determine the gaze-value contribution of the at least one detected occurrence.

19. The system of claim 18, wherein program instructions stored on the non-transitory computer-readable medium and executable by the at least one processor to determine the focus value corresponding to the at least one detected occurrence comprise program instructions stored on the non-transitory computer-readable medium and executable by the at least one processor to:

determine movement of the given advertisement space during the at least one detected occurrence; and use the determined movement of the given advertisement space as a basis to determine the focus value for the at least one detected occurrence.

20. A computer-implemented method comprising:

receiving, by a computing device, first gaze data that is indicative of a wearer-view associated with a first wearable computing device, wherein the wearable computing device is associated with a first user-account;

analyzing, by the computing device, the first gaze data to detect one or more occurrences of one or more advertisement spaces in the first gaze data;

receiving, by the computing device, second gaze data that is indicative of a wearer-view associated with at least one other computing device, wherein the at least one other computing device is also associated with the first user-account;

analyzing, by the computing device, the second gaze data to detect one or more occurrences of one or more advertisement spaces in the second gaze data;

based at least in part on (a) the one or more advertisement-space occurrences detected in the first gaze data, and (b) the one or more advertisement-space occurrences detected in the first gaze data, the computing device determining an individual gaze value for the first user-account; and sending, by the computing device, a gaze-value indication, wherein the gaze-value indication indicates the individual gaze value for the first user-account.

* * * * *